(12) United States Patent
Arvai et al.

(10) Patent No.: US 6,277,867 B1
(45) Date of Patent: Aug. 21, 2001

(54) PESTICIDE COMPOUNDS, COMPOSITIONS AND PROCESS FOR THE PREPARATION THEREOF

(75) Inventors: Geza Arvai, Budapest; Ildiko Bakonyvari, Veszprém; Bela Bertok, Budapest; Laszlo Csiz, Érd; Iren Czudor, Budapest; Zsuzsa R. Kuruczne; Laszlo Pap, both of Érd; Istvan Szekely, Dunakeszi, all of (HU)

(73) Assignee: Chinoin Gyogyszer es Vegyeszeti, Budapest (HU)

( * ) Notice: Subject to any disclaimer, the term of this patent is extended or adjusted under 35 U.S.C. 154(b) by 0 days.

(21) Appl. No.: 09/068,933

(22) PCT Filed: Nov. 19, 1996

(86) PCT No.: PCT/HU96/00069

§ 371 Date: Aug. 31, 1998

§ 102(e) Date: Aug. 31, 1998

(87) PCT Pub. No.: WO97/19040

PCT Pub. Date: May 29, 1997

(30) Foreign Application Priority Data

Nov. 21, 1995 (HU) .................................................. P9503318

(51) Int. Cl.[7] .................. A61K 31/353; A61K 31/4427; C07D 231/12; C07D 307/79; C07D 401/02
(52) U.S. Cl. ....................... 514/326; 514/456; 548/376.1; 546/272.4; 549/365; 549/445; 568/660; 568/681
(58) Field of Search ..................................... 514/456, 469, 514/777, 326; 549/365, 445, 466; 568/660, 662, 681; 548/376.1; 546/272.4

(56) References Cited

U.S. PATENT DOCUMENTS 3,402,179 * 9/1968 Fujimoto et al. .
3,718,686 * 2/1973 Chodnekar et al. .
3,954,793 * 5/1976 Hennessy .

FOREIGN PATENT DOCUMENTS 2 161 163 * 1/1986 (GB) .

OTHER PUBLICATIONS

Sarker et al, J. Agr. Food Chem., 16(5), 1968 pp. 779–786.*

* cited by examiner

Primary Examiner—T. A. Solola
(74) Attorney, Agent, or Firm—Birch, Stewart, Kolasch & Birch, LLP

(57) ABSTRACT

The invention relates to compounds of general formula (I), their optically active isomers and salts wherein Ar=alycylic, aromatic or one or more heteroatom containing heterocyclic moiety, optionally substituted by one or more alkoxy-, methylenedioxy-, alkyl-, halogen-, haloalkyl-,or nitro-group and/or condensed with a benzene ring.

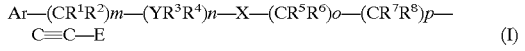

$$\text{Ar}-(CR^1R^2)m-(YR^3R^4)n-X-(CR^5R^6)o-(CR^7R^8)p-C\equiv C-E \quad (I)$$

The compounds of general formula (I) according to the invention can be applied as active ingredients of pesticides, preferably arthropodicide compositions, and as synergists of other arthropodicideactive ingredients.

25 Claims, No Drawings

PESTICIDE COMPOUNDS, COMPOSITIONS AND PROCESS FOR THE PREPARATION THEREOF

This application is the national phase under 35 U.S.C. §371 of prior PCT International Application No. PCT/HU96/00069 which has an International filing date of Nov. 19, 1996 which designated the United States of America, the entire contents of which are hereby incorporated by reference.

This invention relates to alkynyl pesticide compounds of the general formula I., pesticide compositions containing the active ingredients of general formula I., furthermore the pesticide synergists of general formula I., and synergized pesticide compositions with known pesticide active ingredients, and the process for the preparation thereof.

In general formula I the substituents have the following meanings:

Ar=an alicyclic-, aromatic-, or one or more heteroatom containing heterocyclic moiety, optionally substituted by one or more alkoxy, methylenedioxy, alkyl, halogen, haloalkyl or nitro group, and/or condensed with a benzene ring, $R^1$, $R^2$=independently hydrogen, alkyl, alkenyl, haloalkyl, phenyl, substituted phenyl, cycloalkyl, $R^3$, $R^4$=independently hydrogen, alkyl, alkenyl, haloalkyl, phenyl, substituted phenyl, cycloalkyl, or $R^3$, $R^4$ are together=O;

Y=C,=PO, or $YR^3R^4$ form together a

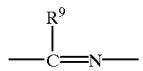

group;

X=—O—; —$NR^{10}$—;

$R^9$=hydrogen, alkyl, phenyl, substituted phenyl;

$R^{10}$=hydrogen, alkyl;

$R^5$, $R^6$, $R^7$, $R^8$ are independently hydrogen, alkyl, alkenyl, haloalkyl, or Ar—$(CR^1R^2)_m$—$(YR^3R^4)_n$—X— form together a carboximide group;

E=hydrogen, halogen, methyl;

m=0, 1, 2;

n=0, 1;

o=0, 1, 2;

p=0, 1, 2, with the proviso that the sum of the atoms or groups of the bridge —$(CR1R^2)_m$—$(CR^3R^4)_n$—X—$(CR^5R^6)_o$—$(CR^7R^8)_p$ is 3 and the —C≡C—E skeleton with the atoms of the bridge forms a linear chain, consisting of 6 atoms ending favorably in a methyl group, furthermore with the proviso that if Ar is naphthyl group. Y means C-atom. X means O-atom. $R^3$ and $R^4$ together can not mean =O.

The invention includes furthermore the salts and the optically active isomers of the compounds of general formula I.

Narrower groups within compounds of general formula I. are represented by the compounds of general formula IA, IB, IC, ID, IE, IF, their salts and optically active isomers, where the meanings of the substituents are the same as defined above.

Favourable representatives of the compounds of general formula I. are:

1-naphthyl-methyl 2-butynyl ether,
2-propynyl-1,3-benzodioxol-5-carboxylate,
1-[(2-butynyloxy)-ethyl]-3,4-dimethoxybenzene,
2,6-dichloro-1-(2-butynyloxymethyl)benzene,
1-[1-(2-butynyloxy)propyl]naphthalene,
R-(+)-2-[1-(2-butynyloxy)ethyl]naphthalene,
5-[(but-2-ynyloxy)methyl]-1,3-benzodioxole,
5-[2-methyl-1-(2-butynyloxy)propyl]-1,3-benzodioxole,
5-[(but-2-ynyloxy)phenylmethyl]-1,3-benzodioxole,
2-[(2-butynyloxy)methyl]-1,4-benzodioxane,
2,3-dihydro-2,2-dimethyl-7-(3-pentyloxy)benzofuran.

In the term Ar the aromatic group is preferably phenyl or naphthyl group, Ar as a heterocyclic moiety may contain one or more O, S, N heteroatoms, it may favourably represent benzodioxole-, benzodioxane-, 2-benzofuran-, 7-benzofuran-moieties.

The alicyclic group may favourably be condensed with a benzene ring, thus for instance may represent indane group, or 1,2,3,4-tetrahydronaphthyl group. The carboximide group may favourably represent phthalimide moiety. The aromatic, heterocyclic and alicyclic Ar groups are optionally substituted by $C_{1-4}$ alkoxy-, methylenedioxy-,$C_{1-4}$ alkyl-, halogen-, $C_{1-4}$ haloalkyl- or nitro group.

Compounds which are non-toxic, or only slightly toxic alone, but given together with a pesticide, preferably arthropodicide agent they enhance markedly the potency of the latter, are called synergists. These materials may in principle act in several ways, however they exert their effect decisively by blocking the metabolism of the active substance. Metabolism may proceed via oxidative, hydrolytic, conjugative and absorption reactions and by the variations thereof. At present there is no unambiguous example for a synergist acting at the receptor level, neither do they play an important role in the praxis.

The synergistic potency e.g. in the case of insecticides is characterized by the so-called SR synergist ratio which is given as follows:

$$SR_{50} = \frac{LD_{50insecticide}}{LD_{50insecticide + synergist}}$$

The more the $SR_{50}$ value differs from 1, the higher is the synergistic potency. The use of synergists in arthropodicidal preparations is very attractive since they afford a possibility to produce new preparations with practically all representatives of the area. These new preparations, compared to the previous ones, promise to be less expensive, less toxic, more selective, encountering less environmental hazard, suppressing the evolution of resistance, and being active also on strains which already evolved resistance.

Following the discovery of synergists and the reveal of their mode of action, a wide-range research and development work started from the mid 60's till the late 70's to work out new synergists. This research, however resulted only a few molecules which really attained application (at present the number of the registered insecticide synergists is less than 10). These compounds are of basic scientific importance in the research of resistance (K. F. Raffa and T. M. Priester. *J. Agric. Entomol.*, 2(1), 27–45, (1985)), however, there are only 2-3 molecules listed as products in the Pesticide Manual, and only two materials (PBO, MGK264) which are actually on the market. The field application has been restricted by several factors: it is not easy to find a chemical tool which can be used selectively and safely, and the cost/effectiveness ratio of which is competitive with that of the active ingredient. To apply a synergist economically, it must be highly potent, it must act at small doses (not exceeding the original dose of the active ingredient).

On the basis of their chemical structures the presently known arthropodicide synergistic compounds may be divided into the following groups:
1,3-methylenedioxyphenyl (MDP) derivatives
O-2-propynyl and propynyl-homologues and their derivatives (ethers, oximethers, esters)
N-alkyl derivatives
phosphor esters
other derivatives e.g. thiocyanates, polyhalo ethers etc.

The compounds may also be divided into groups on the basis of their target of attack [K. F. Raffa and T. M. Priester, *J. Agric. Entomol.*, 2(1), 27–45, (1985)], but this grouping is rather theoretical and less exact, because the actual metabolic processes are not fully known. The metabolism of most of the compounds proceeds consecutively, but may also proceed simultaneously, and may follow several mechanisms. Thus the division is less informative, even if we consider the first step of the cascade degradation as the decisive step.

For the metabolic degradation of most arthropodicides first of all the oxygenase system is responsible. It is agreed in the literature that the compounds of this group exert their activity basically by blocking the cytochrome P450 enzyme of the microsomal oxidation system [John E. Cassida, *J. Agr. Food Chem.*, 18(5), 753–772, (1970), R. M. Sacher. R. L. Metcalf and T. R. Fukuto. *J. Agr. Food Chem.*, 16(5), 779–786, (1968)]. The enzymes forming the structurally analogous group of so-called isoenzymes constitute the major part of the detoxificaton system of the organisms [Ortiz de Montellano. P. R. Ed. *Cytochrome P-450. Structure Mech. and Biochem.*, Plenum New York, (1986)]. They perform detoxification via mono-oxygenation of the substrate, producing a more polar product, which possibly after further transformations can be eliminated by the organism. The system degrades very different structures by the same way. Therefore they are also designated as Mixed Function Oxygenases (MFO) and Polysubstrate Monooxygenases (PSMO).

On that basis one could expect that the surface of the enzyme is aspecific for the synergist, too. Quite the contrary, we have found that the compounds may be optimized.

For the isolation and testing of the Cytochrome P-450 enzymes of insects there are standard methods available [J. G. Scott and S. S. T. Lee; *Arch. Insect Biochem. and Phys.*, 24, 1–19, (1993)]. The enzymes of various species may show great similarities but they may also differ significantly from each other. The synergists known from the literature and investigated by us belong to the group of 0-2-propynyl, and propynyl-homologues and their derivatives (ethers. oxim-ethers esters). As shown by the literature they exhibit different potency for the different species, which means that the oxidation capacity of the species varies to a certain extent. This is the reason for the high insect/mammal selectivity and synergist selectivity, characteristic for that group of compounds. These selectivities, which cannot be directly explained by the above mode of action are the bases of the development and safe application. On the other hand this is the reason why these compounds have not became commercially available. For all the compounds of the group prepared and evaluated so far we can tell, in general, that their effect was exlusively bound to the propynyl side-chain. this chain has been substituted in the allylic position by various aryl rings mainly through an oxygen atom. The compounds known as yet may be divided into the following groups:

Phenyl propargyl ethers [Fellig et. al. *J. Agr. Food Chem.* 18(5). 78. (1970)]
Benzyl propargyl ethers [Ciba Geigy. Ger. Offen. 2 235 005 (1972)]
Benzaidoxime propargyl ethers [Ciba Geigy. Ger. Offen, 2 016 190 (1970)]
Naphthoic acid propargyl esters [Hoffman-La Roche. Belg. Patent. 867 849 (1978)]
Alkynylphthalimides [FMC, Ger. Patent, 1 217 693 (1966)]
Phenyiphosphonic acid propargyl esters [Niagara Chem. Div., FMC Corp., Technical Data Sheet on NIA 16824, (1968)]

The first two groups are sub-divided into further groups owing to the high variability of the aromatic group and its substituents. Thus, there are known naphthyl propargyl ethers [Hoffinan-La Roche, U.S. Pat. No. 3,362,871 (1968); Ciba Geigy, Ger. Offen, 2 100 325 (1971)],
4-hydroxyquinoline propargyl ethers [Alkaloida, HU210 557, (1992)], methylenedioxybenzyl propargyl ethers [Sumitomo. JP, 03 01177, (1973)] and alfa-substituted methylenedioxybenzyl propargyl ethers [Sumitomo, JP, 61 24585, 61 24586 (1986)].

In a study about naphthyl propynyl ethers it has been concluded that butynyl ethersm first of all 3-butynyl ethers are more potent than the analogous propargyl and pentynyl ethers [R. M. Sacher et. al., *J. Agr. Food Chem.* 16, 779–786, (1968)]. Interestingly, however there was no continuation of that work. The discovery has not been patented, either. Detailed analysis of the literature data suggest that the propynyl side-chain cannot be replaced by homologous chains. since the publications and patents relate further on to propargyl derivatives. In order to clear this contraversion we have prepared the compounds in question, and found that in contrast to what was disclosed in the literature, the 2-butynyl derivative (the one ending in a methyl group) is more potent than the 3-butynyl derivative; the alpha-isomers are more potent than the analogous beta-isomers; and the 3-pentynyl derivative is more potent than the 2-butynyl derivative. These data suit well in our theory and the data given in the literature might be the reason why this direction was not followed by others.

Similarily, there is a contraversion regarding the activity of the 4-pentynylphthalimide derivatives: although they proved to be potent synergists of allethrin they antagonized with pyrethrin [H. Jaffe J. L. Neumeyer, *J. Med. Chem.* 13, 901, (1970)]. In these structures again, the alkynyl chain ends in triple bond. The hybride variations of these structures, namely the N-alkyloxy-O-propargyl-phthalimides have also been prepared here again the triple bond is in terminal position [Sumitomo, NL, 6 600 916 (1966)].

To sum up, the most active representatives of the group, although on some tests exhibited outstanding activity, and were superior regarding their synergist/active ingredient ratio [D. J. Henessy, *Biochemical Toxicology of Insecticides*, Ed., R. D. O'Brian & I. Yamamoto, Academic Press, 105–114, (1970)], have never been applied in the praxis. This has several reasons: their activity did not reach the potency of earlier, well-established derivatives, they exhibited activity only in a narrow range, their potency was highly species-dependent, and within one species it depended greatly on the "strength" of the individual. Their safe and broad application was not therefore ensured.

The alkynyl compounds listed above are all derivatives of a common optimal structure, but the authors did not realize the relationships, and have not prepared the most active representatives, alloying and improving the advantages of these groups of compounds.

We have experimentally tested, compared and analysed the biological effect of the known compounds, as well as that of the new derivatives prepared by us, and revealed the structural element which is responsible for the effect. On that basis we have prepared new compounds which surpass significantly the activity of the earlier ones and combine those properties which ensure effectiveness on more species and with more known active ingredients.

The integral part of the present invention is the discovery, that in the optimal compounds the carrier of the activity is a triple bond of an alkynyl structure with an electron-rich Ar ring, which is connected to the triple bond through a mobile bridge consisting of three atoms. The atoms of the bridge are variable and may have substituents, and so is the ring. To enhance the activity it is favourable to introduce lipophilic and electron-rich atoms and substituents. Thus the atoms of the bridge may be beside carbon atoms oxygen, sulphur, nitrogen, and phosphor heteroatoms. These atoms may be linked through single or multiple bonds to each other and optionally with further substituents containing the above heteroatoms they may be substituted to further functional groups or derivatives. The atoms may be replaced by each other. The first element of the bridge may with its substituent form a ring, which may be attached to the aromatic ring, and thus may be part of the electron-rich moiety. Into the ring, linked to the bridge, heteroatoms, as listed above, may also be incorporated, and the effect may be further enhanced by the introduction of alkoxy, halogen, alkyl, haloalkyl or nitro substituents. The ring may be 5-, 6-, or 7-membered and may be condensed with a further ring, which is built according to the above principles, and may incorporate the first element of the bridge. Compounds in which the acetylenic hydrogen of the alkynyl side-chain is replaced by a methyl group exhibit higher activity than the the analogues with terminal triple bond. Keeping these rules we can carry out new substitutions by which we can modify the character of the compounds, according to the demand (lipophilicity, translaminarity, systemicity, etc.) of the application area.

Of the isomers of optically active compounds, e.g. α-methyl-substituted benzyl derivatives the R(+) enantiomers are more potent than the S(−)enantiomers. The difference between the activities of the isomers is growing with an enhancing activity of the racemic mixture.

The compounds developed by us are new, they are characterized by outstanding mammal/insect selectivity and high potency exerted at low dose related to the active ingredient. This is attributed to the outstanding high receptor affinity of our compounds. In comparative experiments the indices of our compounds highly surpassed those of earlier known synergists for active ingredients, whose metabolism is based on microsomal oxidation. This high activity and selectivity were also demonstrated in field studies conducted on small plots. The compounds did not show phytoxicity, they did not separate from the active ingredients, their physico-chemical parameters fitted well with those of the active ingredient. Through these features the doseiefficacyfcost value, which earlier hindered the application, could favourably be modified and the application became possible.

With the active substances of general formula I the effect of the following known arthropodicide active ingredients may favourably be synergized:

Acetamide derivatives: e.g. OXAMYL®; Benzoylurea compounds: e.g. FLUCYCLOXURON®, HEXAFLUMURON®, TEFLUBENZURON®, TRIFLUMURON®; Benzoylurea like IGR compounds; Bicycloheptadiene compounds: e.g. HEPTENOPHOS ; Cross-bridged diphenyl compounds: e.g. ETOFENPROX®, BROMOPROPYLATE®, METHOXYCHLOR®, TEMEPHOS®, TETRADIFON Carbamates: e.g. AMINOCARB®, ALDICARB®, ALDOXYCARB®, ASULAM®, BENDIOCARB®, BENFURACARB®, CARBARYL®, CARBETAMIDE®, CARBOFURAN®, CARBOSULFAN®, DIETHOFENCARB®, DIOXACARB®, ETHIOFENCARB®, FENOBUCARB®, FENOXYCARB®, FURATHIOCARB®, ISOPROCARB®, METHOMYL®, OXAMYL®, PIRIMICARB (PIRIMOR) ®, PROPOXUR®, THIODICARB®, THIOFANOX®, XYLYLCARB®; Carbamoyloxime derivatives: e.g. ALANYCARB®, BUTOCARBOXIM®; Cyclodienes: e.g. ALDRIN®, CHLORDANE®, ENDOSULFAN®, HEPTACHLOR®; Diazoles: FIPRONIL®; Hydrazides: RH 5992®, RH 5849®, CGA 215'944®; Nereistoxin analogues: e.g. BENSULTAPD®; Nitroimidazolidynylenamines: e.g. IMIDACLOPRID®; Organophosphor compounds e.g. QUINALPHOS®, DIAZINON®, PHOSALONE®, DIMETHOATE®, AZINPHOS-METHYL®, Organotin compounds e.g. AZOCYCLOTIN®, CYHEXATIN®, FENBUTATIN OXIDE®;

Phenoxy compounds: e.g. DIAFENTHIURON®; Pyrazoles: e.g. PYRAZOPHOS®; Pyrethroides: e.g. ALLETHRIN®, BIOALLETHRIN®, ESBIOL®, ACRINATHRIN®, FENVALERATE®, EMPENTHRIN®, PRALLETHRIN®, RESMETHRIN®, MTI-800®, FLUFENPROX®, PERMETHRIN®, TETRAMETHRIN®, CYPERMETHRIN®, and their isomers and isomer-combinations; Pyridazinones: e.g. PYRIDABENO®; Pyridine derivatives: e.g. CHLORPYRIPHOSO®; Pyrimidine derivatives: e.g. PYRIMIPHOS-ETHYL®, PYRIMIPHOS-METHYL®; Pyrroles: e.g. AC303-t,630; Quinazolines: e.g. FENAZAQUIN®; Terpenoid derivatives: e.g. METHOPRENE®; Tetrazines: e.g. CLOFENTEZINE®, SzI-121; Thiadiazines: e.g. BUPROFEZIN ; Thiazolidin: pl. HEXYTHIAZOX®; Triazoles: pl. ISAZOPHOS , RH 7988 ; Chlorinated hydrocarbons: LINDANE®; Macrocyclic lactones; TEBUFENPYRAD®; FENPYROXYMATE®; TRIAZAMATE®;

The above known active ingredients are described in the 8th and 10th Edition of the Pesticide Manual, European Patent Application No. 0635499 (SZI-121), A.G.Chem.New Compound review vol. 11(1993) and ACS Symposium Series 504 p. 272. respectively.

Compounds of the general formula I can be most preferably used to synergize the effect of carbamates, preferably carbofuran.

We have found that the compounds have dual action. They are superior synergists of arthropodicide active ingredients, and they also hinder the individual grows of arthropoda through an effect impeding the biosynthesis of ecdison, a material, playing key role in the growth of arthropoda. There is thus an unambiguous relationship between the synergistic- and the individual growth-hindering activities. This latter effect, beside the outstanding metabolism-blocking activity of the compounds, is also a consequence of the fact, that these materals, in contrast to the other, earlier known families of compounds, practically do not degrade or degrade only extremely slowly in the organism of the arthropoda. Thus, when applied alone at a long run, depending on the periods of the endocrin regulation, they are able to block the hormone synthesis and hinder the degradation of the endo and exo-biotica. Due to the toxins accumulating in the organism, the individuals become incapable of living, they do not eat, the production of eggs diminishes, and the reproduction stops.

Beside these enhanced activities, the toxicity values of the compounds on mammals did not increase. This can be attributed to the differences in the electrode potencial values of microsomal oxidation systems for mammals and for arthropoda. Whereas the oxidation potential values of the higher-order organisms are high, and therefore they are able to beat the electron-barrier of the complexed synergists, the oxidation system of the arthropoda, with its small potential, is not capable to oxidate, and by this to remove the complexed molecule from the surface of the enzyme, causing the paralysis of the system. This is the reason why the compounds can be applied safely and selectively. The above-average fast degradation and excretion of the compounds from mammalian owing to their high enzyme activity and fast enzyme binding, ensure, in contrast to the arthropods that these materials do not enhance the effect of biotics found or taken up by the mammalian organism, and therefore they are safe.

The effect was demonstrated by us on various arthropode species. Applied alone, or as a synergist, the compounds were active on insects, plant-lice and also on acari. In the light of the above, this fact refers again to the qualitatively different detoxification system of the mammals.

A very valuable advantage of our compounds is that on applying them to species, which already evolved resistance, the toxic dose could be reduced below the original dose of the known active ingredient (measured on susceptible strains). This has not been experienced with other synergists. This makes possible the safe and effective management of resistent populations, complying with the modern regulations.

Beside the expected advantages mentioned above (they make possible to develop tools which are less expensive, less toxic on mammals selective, and can suppress resistance) with the help of these compounds a number of well-established active ingredients can be renewed, the market of which has fallen in the past years, because resistance evolved against them. (CARBOFURAN®, QUINALPHOS®, CARTAP®, METHOMYL®). Our compounds create new application and market possibilities, since they enhance the potency of less active materials (RESMETHRIN, BIOALLETHRIN, PRIRIMICARB, etc.) to the level of the most active compounds, without increasing their toxicity. PBO, which is on the market in big lots, but—with natural resources running low at increasing price, and which is being withdrawn because of its suspected tumor provoking effect, may also be replaced with the help of our compounds.

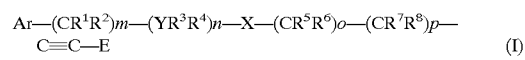

(I)

The preparation of the compounds of general formula I varies depending on the different groups of compounds, and can be carried out by the chemical methods, characteristic for the preparation of these groups.

Thus a.) For the Preparation of Compounds of General Formula IA, (IA)

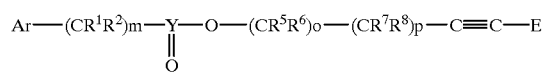

where Ar, $R^1$, $R^2$, $R^5$, $R^6$, $R^7$, $R^8$, Y, E, m, o and p have the same meanings as defined above; compounds of general formula II and III are reacted (II)

(III)

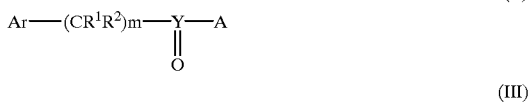

wherein Ar, $R^1$, $R^2$, $R^5$, $R^6$, $R^7$, $R^8$, Y, E, m, o and p have the same meanings as defined above, and A and B are groups suitable to form an ester bond.

b.) For the Preparation of Compounds of General Formula IB, (IB)

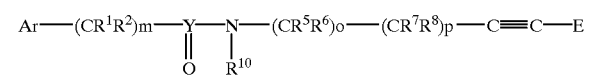

where Ar, $R^1$, $R^2$, $R^5$, $R^6$, $R^7$, $R^8$, $R^{10}$, Y, E, m, o and p have the same meanings as defined above; compounds of general formula IV and V are reacted (II)

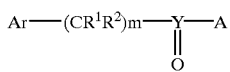

-continued

(III)

wherein Ar, $R^1$, $R^2$, $R^5$, $R^6$, $R^7$, $R^8$, Y, E, m, o and p have the same meanings as defined above, and C and D stand for groups suitable to form an amide bond.

c.) For the preparation of compounds of general formula IC,

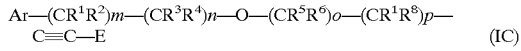
(IC)

where Ar, $R^1$, $R^2$, $R^5$, $R^6$, $R^7$, $R^8$, E, m, o and p have the same meanings as defined above, and $R^3$ and $R^4$ may independently mean H, alkyl, alkenyl, haloalkyl, phenyl, or substituted phenyl, compounds of general formula VI and VII are reacted,

(VI)

(VII)

wherein Ar, $R^1$, $R^2$, , $R^5$, $R^6$, $R^7$, $R^8$, E, m, o and p have the same meanings as defined above, $R^3$ and $R^4$ may independently mean H, alkyl, alkenyl, haloalkyl, phenyl, or substituted phenyl, and F and G stand for groups suitable to form an ether bond.

d.) For the preparation of compounds of general formula ID, (ID)

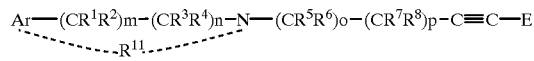

wherein Ar—$(CR^1R^2)m$—$(CR^3R^4)n$—N— stand for carboximide group, $R^5$, $R^6$, $R^7$, $R^8$, E, o, and p have the same meanings as defined above, and $R^{11}$ is a carbonyl group, a carboximide of general formula VIII is reacted with a compound of general formula IX,

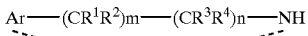
(VIII)

(IX)

wherein $R^5$, $R^6$, $R^7$, $R^8$, E, o, and p have the same meanings as defined above and Lg stands for a leaving group.

e.) For the preparation of compounds of the gene ral formula IE, (IE)

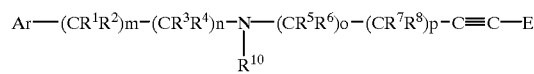

where Ar, $R^1$, $R^2$, $R^3$, $R^4$, $R^5$, $R^6$, $R^7$, $R^8$, $R^{10}$, E, m, n, 0 and p have the same meaning as defined above, compounds of the general formula X and XI are reacted,

(X)

(XI)

wherein Ar, $R^1$, $R^2$, $R^3$, $R^4$, $R^5$, $R^6$, $R^7$, $R^8$, $R^{10}$, E, m, n, o and p have the same meaning as defined above, and H and I stand for groups suitable to form a group.

f.) For the preparation of compounds of general formula IF, (IF)

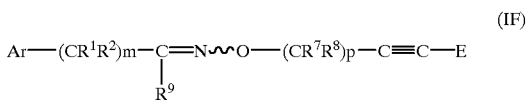

where Ar, $R^1$, $R^2$, $R^3$, $R^4$, $R^5$, $R^6$, $R^7$, $R^8$, $R^9$, E, m, n, o and p have the same meaning as defined above, compounds of the general formula XII and IX are reacted (XII)

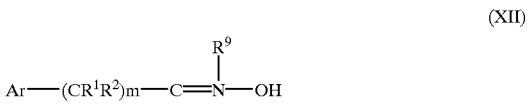

(IX)

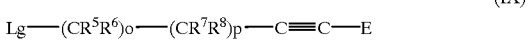

wherein Ar, $R^1$, $R^2$, $R^3$, $R^4$, $R^5$, $R^6$, $R^7$, $R^8$, $R^9$, E, m, n, o and p have the same meaning as defined above, and Lg stands for a leaving group.

If desired, the compound of general formula I can be transformed into its salts, or it may be liberated from its salts. If desired, the optically active isomers of the compound of general formula I can be separated.

To prepare the compounds of general formula I advantageously:

a.) The acyl halide of general formula II is reacted with the alkynol of general formula III, or the carboxylic acid of general formula II is reacted with the alkynyl halogenide of general formula III, in the presence of an acid binding agent, or the carboxylic acid of general formula II is reacted with the alkynol of general formula III in the presence of an activator, preferably diethyl azodicarboxylate and triphenylphosphine or dicyclohexylcarbodiimide and an acidic catalyst, b.) The acyl halide of general formula II is reacted with the primary or secondary alkynylamine of general formula V, or the carboxamide of general formula IV is reacted with the alkynyl halogenide of general formula V, optionally in the presence of an acid-binding agent, c.) The alcohol of general formula VI is reacted with the alkynyl halogenide of general formula VII, or the halogenide of general formula VI is reacted with the alkynol of general formula VII in the presence of a base, or the alcohol of general formula VI and the alkynol of general formula VII are reacted in the presence of an activator, preferably diethyl azodicarboxylate and triphenylphosphine or dicyclohexylcarbodiimide and an acidic catalyst, d.) The carboximide of general formula VIII is reacted in the presence of a base with the alkynyl halogenide or -mesylate, -tosylate, -trifluoroacetate of general formula IX, or e.) The secondary amine of general formula X is reacted with the alkynyl halogenide of general formula XI. or the halogenide of general formula X is reacted with the secondary amine of general formula XI in the presence of a base, or f.) The aldoxime or ketoxime of general formula XII is reacted in the presence of a base with the alkynyl halogenide or -mesylate, -tosylate, -trifluoroacetate of general formula IX.

The compounds prepared and claimed by us are new they are not disclosed in the literature. Their structures have been elucidated after purification, purity was checked by TLC and GC methods. The molecular formula of the compounds was proven by elementary analysis and the structures were unequivocally supported by IR, 1H- and 13C-NMR measurements.

The materials can be formulated as independent compositions or in admixture with other known arthropodicide active ingredients, and according to the application goal known carriers and other auxiliary materials may be used. Thus, by methods known per se. emulsion concentrates, microemulsions, dusters, aerosols, vaporizers and smokers may be prepared. [Rhone Poulenc-Geronazzo: Surfactant and Specialities for Plant Protection., Application Manual (1994). ICI: Surfactants. Application Manual (1992)].

In the course of the application the preparation containing the compound of general formula I and the preparation containing the known active ingredients(s) can be used one after the other or by making a tank-mixture of them.

To demonstrate the scope of our invention we present the following examples. without limiting the scope to the examples.

EXAMPLES FOR PREPARATION

Purity of the compounds was checked by TLC and GC methods: (CP 9000, CP-SIL-5CB. 60 m×0.53 μm. 5 m/min $N_2$, FID, 220° C.). As shown by these methods all compounds had purity over 95%. Structure of the materials was supported by IR, 1H and C13-NMR measurements, molecular formulae were proven by elementary analysis.

1. Alkynyl Esters

General Procedure

A.)

The appropriate alkynyl alcohol was dissolved in dry benzene, pyridine was added and the mixture was cooled to 0-50C. To this mixture the acyl chloride was added at a rate that the inner temperature does not exceed 5° C. The reaction mixture was stirred at room temperature overnight, the precipitated pyridinium hydrochloride was filtered off. The filtrate was neutralized with hydrogen chloride solution, then washed subsequently with water and saturated sodium chloride solution, dried on $MgSO_4$ and evaporated. The raw material was purified by chromatography.

B.)

6 mmol of the acide were dissolved in 20 ml of dry THF and 1,0 g (6 mmol) of diethyl azodicarboxylate (DEAD) were added. The mixture was cooled on an ice-water bath, and the solution of 10 mmol of the alkynol and 1.6 g (6 mmol) of triphenylphosphine in 10 ml of THF was added. The characteristic orange colour of the DEAD gradually disappeared. The solution was stirred at room temperature overnight, then it was diluted with 50 ml of ethyl acetate, washed with saturated sodium chloride solution, dried and evaporated. From the residue the triphenyiphosphine oxide crystallized on addition of hexane-ethylacetate mixture. The filtrate was purified by coloumn chromatography.

|  | Compound | Mp (C.°) | IR ν (cm$^{-1}$) | 1H-NMR δ (ppm) | 13C-NMR δ (ppm) |
|---|---|---|---|---|---|
| 1.1 501 | 2-Propynyl 1,3-benzodioxol-5-carboxylate | 69–70 | 3270, 3010, 2922, 2853, 2124, 1726, 1625, 1606, 1501, 1445, 1373, 1279, 1263, 1157, 1103, 1076, 1039, 762. | 2.51 (1H, t, J=2.4 Hz, ≡C—H), 4.88 (2H, d, J=2.4 Hz, OCH$_2$—C≡), 6.03 (2H, s, OCH$_2$O), 6.83 (1H, d, J=8.2 Hz), 7.47 (1H, d, J=1.6 Hz), 7.66 (1H, dd, J=8.2, 1.6 Hz | 52.34 (OCH$_2$—C≡), 74.92 (≡CH), 77.81 (OCH$_2$—C≡), 101.85 (OCH$_2$O), 107.99, 109.59 (C-4, C-7), 123.29 (C-5), 125.71 (C-6), 147.74 (C-3a), 151.91 (C-7a), 165.07 (CO ester) |
| 1.2 502 | 2-Butynyl 1,3-benzodioxol-5-carboxylate | 63–64 | 3016, 2959, 2920, 2244, 1714, 1626, 1606, 1508, 1450, 1372, 1276, 1240, 1163, 1117, 1078, 1036, 970, 925, 758. | 1.86 (3H, t, J=2.3 Hz, ≡C—CH$_3$), 4.84 (2H, q, J=2.3 Hz, OCH$_2$—C≡), 6.03 (2H, s, OCH$_2$O), 6.83 (1H, d, J=8.2 Hz), 7.47 (1H, d, J=1.6 Hz), 7.67 (1H, dd, J=8.2, 1.6 Hz). | 3.65 (≡C—CH$_3$), 53.19 (OCH$_2$—C≡), 73.33 (OCH$_2$—C≡), 83.17 (≡C—CH$_3$), 101.81 (OCH$_2$O), 107.95, 109.62 (C-4, C-7), 123.69 (C-5), 125.62 (C-6), 147.72 (C-3a), 151.78 (C-7a), 165.33 (CO ester) |

2. Alkynyl-amides

General Procedure

The solution of the acyl chloride was reacted with the solution of the alkynylamine, in the presence of pyridine, at room temperature. The suspension was diluted washed consecutively with water, diluted hydrochloric acid solution and sodium hydrocarbonate solution, dried, evaporated and purified by chromatography and crystallisation.

| | Compound | Mp (C.°) | IR ν (cm$^{-1}$) | 1H-NMR δ (ppm) | 13C-NMR δ (ppm) |
|---|---|---|---|---|---|
| 2.1 523 | N-(2-butynyl) 3,4-methylene-dioxy-benzamide | 143–144 | 3334, 3075, 2918, 1641, 1620, 1605, 1546, 1500, 1485, 1313, 1264, 1239, 1042. | 1.82 (3H, t, J=2.4 Hz, CH$_3$—C≡), 4.16 (2H, m, NH—CH$_2$—C≡), 6.02 (2H, s, (CH$_2$O)$_2$), 6.23 (NH), 6.81 (1H, dd, J=0.6, 7.8 Hz, H-4), 7.28–7.34 (2H, m, H-6, H-7) | 3.54 (CH$_3$—C≡), 30.37 (NH—CH$_2$—C≡), 74.72 and 79.77 (C≡C), 101.73 (OCH$_2$O), 107.72, 108.02 (C-4, C-7), 121.70 (C-6), 128.26 (C-5), 148.01 (C-3a), 150.49 (C-7a), 166.37 (CONH) |
| 2.2 535 | N-(2-Butynyl)-2-naphthamide | 133–134 | 3295 (NH), 3055, 2922, 2913, 2850, 1641, 1629, 1602, 1541, 1414, 1309, 776, 756 | 1.08 (3H, t, J=2.1 Hz, CH$_3$—C≡), 3.38 (1H, s, NH), 4.10 (2H, m, CH$_2$—C≡), 7.60 (2H, m), 8.0 (3H, m), 8.49 (1H, s, H-1), 9.03 (1H, t, J=5.3 Hz) | 3.27 (CH$_3$—C≡), 29.11 (—CH$_2$—C≡), 76.77 and 78.07 C≡C), 124.29 (C-3), 126.90, 127.82 (three signals overlapping), 128.08, 129.07, 131.51 (C-4a), 132.32 (C-2), 134.37 (C-8a), 166.07 (CO) |
| 2.3 541 | N-(2-Propynyl)-1-naphthamide | 105–106 | 3229 (NH), 3046, 2963, 2927, 2118, 1635, 1618, 1590, 1576, 1531, 1415, 1301, 1245, 1033, 788, 773, 759, 519 | 2.27 (3H, t, J=2.4 Hz, H—C≡), 4.24 (2H, q, J=2.4, CH$_2$—C≡), 6.52 (1H, broad s, NH), 7.35 (1H, t, J=8.1 Hz), 7.50 (3H, (1H, m) | 29.62 (—CH$_2$—C≡), 71.80 (H—C≡C), 79.43 (H—C≡C), 124.59, 125.19, 128.28, 130.06 (C-8a), 130.85 (C-2), 133.34 (C-1), 133.59 (C-4a), 169.14 (CO) |
| 2.4 542 | N-(2-Butynyl)-1-naphthamide | 120–122 | 3276 (NH), 3046, 3011, 2917, 2856, 1632, 1618, 1591, 1577, 1522, 1444, 1432, 1287, 1258, 783 | 1.83 (3H, t, J=2.1 Hz, CH$_3$—C≡), 4.25 (2H, q, J=2.1 Hz, CH$_2$—C≡), 6.25 (1H, s, NH), 7.31–7.60 (3H, m), 7.85 (2H, m), 8.32 (1H, m) | 3.50 (CH$_3$—C≡), 30.24 (—CH$_2$—C≡), 74.47 and 79.81 (C≡C), 124.59, 125.19, 124.62, 125.09, 125.37, 126.39, 127.10, 128.26, 130.11 (C-8a), 130.75 (C-2), 133.64 and 133.75 (C-1, C-4a), 169.03 (CO) |

3. Alkynylimides

General Procedure

To the solution of phthalimide in dry DMF 1 molar equivalent of dry potassium carbonate was added and to this suspension was added dropwise the toluene solution of 1 molar equivalent of alkynyl bromide. The suspension was stirred at 80° C. for 3 hours, then it was poured on ice-water the crystals were collected and crystallized from 96% ethanol.

4. (Aryl-alkyl)-, Alkyl-alkynyl Ethers 4.0 Preparation of 1-[(2-butynyloxy)-ethyl]-3,4-dimethoxybenzene (Compound 599)

In a 50 ml flask fitted with thermometer, magnetic stirrer, addition funnel, and connected to an inert gas system the suspension of 30 ml of dry THF and 1.5 g (0.063 mol) of NaH (cca.90%) was prepared. To the suspension was added dropwise at room temperature the solution of 4.0 g (0.021 mol) of α-methyl-veratrylalcohol in 21 ml of dry THF. The

| | Compound | Mp (C.°) | IR ν (cm$^{-1}$) | 1H-NMR δ (ppm) | 13C-NMR δ (ppm) |
|---|---|---|---|---|---|
| 3.1 537 | N-(But-2-ynyl)-phthalimide | 216–218 | 3090, 3040 (H—C aromatic), 2957, 2920 (CH aliphatic), 2234 (C≡C) 1768, 1718 (CO), 1609 (C≡C aromatic), 1468, 1431, 1397, 1354, 1333, 1126, 1090, 952, 775, 732, 712, 629, 560, 532. | 1.76 (3H, t, J=2.3 Hz, CH$_3$—C≡), 4.32 (2H, q, J=2.3 Hz, N—CH$_2$—C≡), 7.86–7.91 (4H, m, aromatic) | 3.12 (CH$_3$—C≡), 27.16 (N—CH$_2$—C≡), 73.82 (CH$_3$—C≡), 79.06 (CH$_2$—C≡), 123.48 (C-3, C-6), 131.64 (C-1, C-2), 134.87 (C-4, C-5), 167.01 (CO) | mixture was heated under reflux conditions for 1 hour, cooled to room temperature, 4.1 g (0.0315 mol) of 1-bromo-2-butyn were added, then the heating was continued. The reaction was followed by TLC (eluent: hexane-EtOAc 4:1). The reaction is completed in about 3–4 hours.

To the cooled thick suspension 50 ml of ether was added, the mixture was filtered on Celite, the filtrate was washed with distilled water, dried on magnesium sulfate and evaporated. The residual oil was purified by coloumn chromatography (eluent: hexane-EtOAc 4:1, $R_f$=0.37).

Yield: 2.3 g (9.8 mmol), 46.9%.

Purity of the product was checked by GC analysis: (CP 9000. CP-SIL-5CB, 60 m×0.53 μm, 5 ml/min $N_2$, FID, 250° C.) $t_R$=12.0 min, >99%

Proof of Structure:

Elementary analysis: ($C_{14}H_{17}O_3$, 233.29):
calculated: C% 72.08, H% 7.35
found: C% 69.70, H% 7.21

IR ($CHCl_3$) ν $cm^{-1}$: 2976, 2855, 2837, 1605, 1595, 1514, 1465, 1419, 1371, 1353, 1311, 1260, 1164, 1141, 1086, 1027, 864

$^1$H-NMR (200 MHz, $CDCl_3$) δ: 1.46 (3H, d, J=6.5 Hz, CH—$CH_3$), 1.85 (3H, t, J=2.3 Hz, ≡C—$CH_3$), 3.83 and 4.01 (2H, $ABX_3$ $J_{AB}$=15.0 Hz, $J_{AX}$=$J_{BX}$=2.3 Hz, ≡C—$CH_2$O), 3.87 and 3.89 (summa 6H, s each $OCH_3$) 4.55 (2H, q, J=6.5 Hz, Ar—CHO), 6.80–6.89 (3H, m, aromatic).

$^{13}$C-NMR (50 MHz, $CDCl_3$)δ: 3.61 (≡C—$CH_3$), 23.76 (CH—$CH_3$), 55.87 ($OCH_3$). 55.96 (≡C—$CH_2$O). 75.36 (≡C—$CH_2$), 76.40 (Ar—CH—$CH_3$), 81.91 (≡C—$CH_3$), 109.06 (C-2), 110.86 (C-5), 118.94 (C-6), 135.30 (C-1), 148.52 (C-3), 149.19 (C4).

In an analogous way as described in Example 4.0 were prepared the following compounds:

| | Compound | Mp (C. °) | IR ν($cm^{-1}$) | 1H-NMR δ (ppm) | 13C-NMR δ (ppm) | $[α]_D^{20}$ |
|---|---|---|---|---|---|---|
| 4.1 279 | 1-naphthyl-methyl 2-butynyl ether | oil | 3044, 3001, 2945, 2920, 2854, 1598, 1509, 1356, 1166, 1086, 1067 | 1.93(3H, t, J=2.3 Hz, C≡C—$CH_3$), 4.22(2H, q, J=2.1 Hz, O—$CH_2$—C≡C), 5.06(2H, s, $C_{10}H_7$—$CH_2$—O), 7.45(1H, t, J=8 Hz), 7.53(3H, m), 7.84(1H, d, J=8.1 Hz), 7.88(3H, m), 7.88(1H, d, J=7.7 Hz), 8.19(1H, d, J=8.2 Hz) | 3.6(C≡C—$CH_3$), 57.71 (O—$CH_2$—C≡C), 69.72 $C_{10}H_7$—$CH_2$—O), 75.10 (O—$CH_2$—C≡C), 82.76 (O—$CH_2$—C≡C), 124.03, 125.10, 125.72, 126.19, 126.85, 128.43, 128.72, 131.79(C-8a), 133.06, 133.70 | |
| 4.2 292 | 1-[1-(2-butynyloxy)-ethyl]-naphthalene | oil | 3052, 2977, 2921, 2856, 1596, 1509, 1444, 1371, 1095, 1078 | 1.67(3H, d, J=6.5 Hz, $CH_3$—CH), 1.87(3H, t, J=2.3 Hz, ≡C—$CH_3$), 2.96 and 4.15 (summa 2H, ABX, $J_{AB}$=15.0 Hz, $J_{AX}$-$J_{BX}$=2.3 Hz, $OCH_2$—CvC), 5.40(1H, q, J=6.5 Hz, $C_{10}H_7$—CH—O), 7.51(3H, m), 7.61(1H, d, J=6.8 Hz), 7.79(1H, d, J=8.1 Hz), 7.89(1H, dd, J=7.9, 1.8 Hz), 8.22(1H, d, J=8.1 Hz) | 3.64(C≡C—$CH_3$), 22.96 ($CH_3$—CH), 56.37 (O—$CH_2$—C≡C), 74.29($CH_3$—CH), 75.36 and 82.14 (C≡C) 123.26(C-8), 123.52, 125.50, 125.85, 127.92, 128.83, 130.78 (C-8a), 133.88(C-4a), 138.42(C-1) | |
| 4.3 454 | 1-[1-(2-butynyloxy)-propyl]-naphthalene | oil | 3058, 3048, 3000, 2962, 2932, 2923, 2876, 2856, 1598, 1509, 1460, 1105, 1062. | 1.02(3H, t, J=7.4 Hz, $CH_3$—$CH_2$), 1.89(3H, t, J=2.3 Hz, C≡C—$CH_3$), 2.03(2H, m, $CH_3$—$CH_2$), 3.95 and 4.17 (summa 2H, ABX, $J_{AB}$=15.0 Hz, $J_{AX}$=$J_{BX}$=2.3 Hz, $OCH_2$—C≡C), 5.15(1H, t, J=6.4 Hz, $C_{10}H_7$—CH—O), 7.53(3H, m), 7.59 (1H, d), 7.81(1H, d, 7.89(3H, m), 8.27(1H, d) | 3.59(C≡C—$CH_3$), 10.62 ($CH_3$—$CH_2$), 30.27 ($CH_3$—$CH_2$), 56.54 (O—$CH_2$—C≡C), 75.50 (O—$CH_2$—C≡C), 80.08 and 81.96(OCH-naphthyl and O—$CH_2$—C≡C), 123.43(C-8), 124.40, 125.31, 125.36, 125.73, 127.91, 128.79, 131.19 (C-8a), 133.88(C-4a), 137.12(C-1) | |
| 4.4 472 | 1-[2-methyl-1-(2-butynyloxy)-propyl]-naphthalene | oil | 3051, 2959, 2922, 2871, 1598, 1509, 1466, 1064. | 0.87 and 1.16 (summa 6H, d each, J=6 Hz, $CH(CH_3)_2$), 1.88(3H, t, J=2.3 Hz, C≡C—$CH_3$), 2.31(1H, m, $CH(CH_3)_2$), 3.89 and 4.14(2H summa $ABX_3$, $J_{AB}$=15 Hz, $J_{AX}$=$J_{BX}$=2.3 Hz, $OCH_2$), 4.92(1H, d, J=6 Hz, CH—O), 7.53(4H, m), 7.83(1H, d, J=8 Hz), 7.91(1H, dd, J=7, 2 Hz), 8.30(1H, d, J= 7.6 Hz) | 3.57(C≡C—$CH_3$), 19.87 and 18.77($CH(CH_3)_2$), 34.20($CH(CH_3)_2$), 56.71($OCH_2$), 75.67 (C≡C—$CH_3$), 81.77 (C≡C—$CH_3$), 123.84(C-8) 125.15, 125.31, 125.39, 125.60, 127.91 (C-4), 128.76(C-5), 131.74(C-8a), 133.87 (C-4a), 136.56(C-1) | |
| 4.5 389 | 1-[(1-methyl-(2-propynyloxy)-methyl]-naphthalene | oil | 3306, 3049, 2990, 2935, 2866, 1599, 1510, 1447, 1374, 1327, 1099, 1064 | 1.51(3H, d, J=6 Hz), $CH_3$; 2.56(1H, d, J=2 Hz), CH; 4.30(H, qxd J=6.2 Hz)OCH; 4.91 | 22.1, $CH_3$, 64.25, OCH; 68.99, CH; 73.34, aryl—$CH_2$; 83.71, CH—C; 124.11, C-8; 125.17, C-2; | |

-continued

| | Compound | Mp (C. °) | IR ν(cm⁻¹) | 1H-NMR δ (ppm) | 13C-NMR δ (ppm) | $[\alpha]_D^{20}$ |
|---|---|---|---|---|---|---|
| | | | | and 5.34(2H, AB, $J_{AB}$= 15 Hz)OCH₂; 7.46 (1H, dd, J=7.8 Hz), 7.54 (3H, m), 7.86(2H, m), 8.18(1H, mxd, J=6 Hz) aromatic | 125.74, C-3; 126.18, C-6, 126.92, C-7; 128.47, C-4; 128.75, C-5; 131.88. C-8a, 133.20, C-4a; 133.77, C-1 | |
| 4.6 256 | 2-[1-(2-propynyloxy)-ethyl]-naphthalene | oil | 3307, 3000, 2979, 2929, 2857, 1603, 1505, 1442, 1373, 1311, 1270, 1215, 1087, 1055, 860, 821, 633 | 1.58(3H, d, J=6.5 Hz, CH₃—CH), 2.44(1H, t, J=2.4 Hz) CH, 3.92 (1H, dd, J=2.4, 15.7 Hz) OCH$_a$—C≡C, 4.13(1H, dd, J=2.4, 15.7 Hz), OCH$_b$—C≡C, 4.84(1H, q, J=6.5 Hz, C₁₀H₇—CH—O), 7.50(3H, m), 7.77(1H, s), 7.85(3H, m | 23.66(CH₃—CH), 55.55 (O—CH₂—C≡C), 74.07 and 76.80(CH—O, CCH), 79.98, (CCH), 124.11, (C-6), 125.60 (C-7), 125.90, 126.15, 127.68, 127.85, 128.5, 133.16, 133.21, 139.75 (C-1) | |
| 4.7 293 | 2-[1-(2-butynyloxy)-ethyl]-naphthalene | oil | 3051, 2977, 2920, 2854, 1602, 1444, 1084 | 1.57(3H, d, J=6.5 Hz, CH₃—CH), 1.87(3H, t, J=2.3 Hz, CH₃—C), 3.90 and 4.08(1-1H, ABX3, J=15, 2.3 Hz, OCH$_{a,b}$—C≡C), 4.79(1H, q, J=6.5, C₁₀H₇—CH—O), 7.49(3H, m), 7.77(1H, bs, H-1), 7.85(3H, m) | 3.64(C≡C—CH₃), 23.78 (CH₃—CH), 56.23 (O—CH₂—C≡C), 75.28 (C≡C—CH₃), 76.72 (CH—CH₃), 82.10 (C≡C—CH₃), 124.14, (C-6), 125.42, 125.78, 126.05, 127.64, 127.80, 128.40, 133.07(C-4), 133.19 (C-8), 140.14(C-2) | |
| 4.8 441 | 5-[(But-2-ynyloxy)-methyl]-1,3-benzodioxole | oil | 2997, 2946, 2921, 2888, 2376, 1609, 1503, 1491, 1445, 1251, 1099, 1070, 1042, 937, 865, 810 | 1.87(3H, t, J=2.3 Hz, Me), 4.10(2H, q, J=2.3 Hz, O—CH₂—C≡), 4.47, (2H, s, O—CH₂—Ar), 5.94(2H, s, O—CH₂—O), 6.76(1H, d, J=8 Hz, H-7), 6.81(1H, dd, J=8.15 Hz, H-6), 6.86(1H, J=1.5 Hz, H-4) | 3.52(Me), 57.29 (O—CH₂—C≡), 71.15 (O—CH₂—Ar), 82.54 (CH₃—C≡), 100, 9 C-2, 107.95, 108.71(C-4,7), 121.66(C-6), 131.39, (C-5), 147.15, 147.66(C3a, C-7a) | |
| 4.9 484 | 5-[2-Methyl-1-(2-butynyloxy)-propyl]-1,3-benzodioxole | oil | 2958, 2921, 2874, 1608, 1502, 1486, 1441, 1076, 1041, 940 | 0.63 and 0.94 (summa 6H, d each, J=6.8 Hz, CH(CH₃)₂), 1.76(3H, t, J=2.3 Hz, C≡C—CH₃), 1.81(1H, m, CH(CH₃)₂), 3.69 and 3.94(summa 2H, ABX₃, $J_{AB}$=15.1 Hz, $J_{AX}$=$J_{BX}$=2.3 Hz OCH₂), 3.86(1H, d, J=7.8 Hz, CH—O), 5.87 (2H, AB, OCH₂O), 6.62(1H, dd, J=7.9, 1.6 Hz, 6-H), 6.68(1H, d, J=7.9 Hz, 7-H), 6.71(1H, d, J=1.6 Hz, 4-H) | 3.58(C≡C—CH₃), 18.93 and 19.30((CH(CH₃)₂), 34.42(CH(CH₃)₂), 56.20(OCH₂), 75.48(C≡C—CH₃), 81.66(C≡C—CH₃), 86.25(CH—O), 100.85(OCH₂O), 107.44, 107.63(C-4, 7) 121.29(C-6), 134.48(C-5), 146.88 and 147.63(C-3a, 7a) | |
| 4.10 554 | 5-[(But-2-ynyloxy)-cyclohexyl-methyl]-1,3-benzodioxole | oil | 2920, 2877, 2851, 1610, 1502, 1485, 1441, 1357, 1243, 1132, 1064, 1040, 942. | 0.84–1.31(6H, m), 1.50–1.77(4H, m) 1.83(3H, t, J=2.3 Hz, ≡C—CH₃), 2.08(1H, m, H-1'), 3.76 and 4.01 (ABX₃, $J_{AB}$=15 Hz, $J_{AX}$=$J_{BX}$=2.3 Hz, OCH₂), 3.98(1H, d, J=8.3 Hz, CH—O), 5.97 (2H, s, OCH₂O), 6.65–6.78(3H, m). | 3.64(C≡C—CH₃), 25.93 and 26.05(C-2', C-6'), 26.52(C-3), 29.25 and 29.86(C-3', C-5'), 43.97 (C-1'), 56.19(OCH₂), 75.57(C≡C—CH₃), 81.64(C≡C—CH₃), 85.45(CH—O), 100.88(OCH₂O), 107.47 and 107.64(C-4, C-7), 121.31(C-6), 134.48(C-5), 146.91 and 147.69(C-3a, C-7a). | |
| 4.11 555 | 5-[(But-2-ynyloxy)-phenyl-methyl]-1,3-benzodioxole | oil | 2993, 2887, 2859, 1605, 1502, 1486, 1442, 1357, 1239, 1037, 937. | 1.89(3H, t, J=2.3 Hz, ≡C—CH₃), 4.12(2H, q, J=2.3 Hz, OCH₂), 5.56 (1H, s, CH—O), 5.93 (2H, s, OCH₂O), 6.74–6.86(3H, m), 7.25–7.39 (5H, m) | 3.69(C≡C—CH₃), 56.34 (OCH₂), 75.12 (C≡C—CH₃), 81.23 (C≡C—CH₃), 82.56 (CH—O), 100.99 (OCH₂O), 107.78 and 107.95(C-4, C-7), 120.98(C-6), 127.01 (C-2', C-6'), 127.50(C-4), 128.36(C-3', C-5'), 135.54(C-5), 141.62 (C-1'), 147.05 and | |

| | Compound | Mp (C. °) | IR ν(cm⁻¹) | 1H-NMR δ (ppm) | 13C-NMR δ (ppm) | $[\alpha]_D^{20}$ |
|---|---|---|---|---|---|---|
| 4.12 493 | (2-Butynyloxy-methyl)-3,4-dimethoxy-benzene | oil | 3025, 3000, 2956, 2937, 2921, 2855, 2839, 1607, 1595, 1512, 1466, 1443, 1420, 1158, 1140, 1070, 1028 | 1.84(3H, t, J=2.3 Hz, C≡C—CH₃), 3.83 and 3.35(summa 6H, CH₃O), 4.08(2H, q, J=2.3 Hz, OCH₂C≡C—), 4.48(2H, s, aryl—CH₂), 6.77–6.88(3H, m, aryl) | 147.83(C-3a, C-7a) 3.45(C≡C—CH₃), 55.67 and 55.71(CH₃O), 57.31(OCH₂C≡C—), 71.22(aryl—CH₂), 75.0 (C≡C—CH₃), 82.42 (C≡C—CH₃), 110.76(C-2), 111.23(C-5), 120.54 (C-6), 130.05(C-1), 148.58(C-4), 148.88 (C-3). | |
| 4.13 503 | 2,6-Dichloro-1-(2-butynyloxy-methyl)-benzene | oil | 2931, 2918, 2881, 2849, 2241, 1584, 1563, 1473, 1356, 1198, 1157, 1091, 1073, 787, 769 | 1.87(3H, t, J=2.3 Hz, ≡C—CH₃), 4.21(2H, q, J=2.3 Hz, OCH₂—C≡), 4.83(2H, s, C₆H₄Cl₂—O—CH₂), 7.17(1H, dd, J=9.1, 6.7 Hz), 7.31 (2H, m) | 3.64(≡C—CH₃), 58.68 (OCH₂—C≡), 66.15 (C₆H₄Cl₂—O—CH₂), 74.94(OCH₂—C≡), 82.81(≡C—CH₃), 128.33(C-3, C-5), 129.96(C-4), 133.17 (C-2, C-6), 136.97(C-1) | |
| 4.14 498 | 1-(2-Butynyloxy)-1,2,3,4-tetrahydro-naphthalene | oil | 2998, 2941, 2860, 1604, 1489, 1440, 1070, 1044 | 1.84(3H, t, J=2.3 Hz, C≡C—CH₃), 3.83 and 3.85(summa 6H, CH₃O), 4.08(2H, q, J=2.3 Hz, OCH₂C≡C—), 4.48(2H, s, aryl—CH₂), 6.77–6.88(3H, m, aryl) | 3.45(C≡C—CH₃), 55.67 and 55.71(CH₃O), 57.31(OCH₂C≡C—), 71.22(aryl—CH₂), 75.0 (C≡C—CH₃), 82.42 (C≡C—CH₃), 110.76 (C-2), 111.23(C-5), 120.54(C-6), 130.05(C-1), 148.58(C-4), 148.88 (C-3) | |
| 4.15 479 | 1-(2-Butynyloxy)-indane | oil | 3073, 3000, 2938, 2924, 2854, 2243, 1711, 1667, 1608, 1461, 1332, 1097, 1063, 1018 | 1.91(3H, t, J=2.3 Hz, C≡C—CH₃), 2.15(1H, dddd, J=13.2, 8.4, 4.8, 3.8 Hz, 2-H), 2.37(1H, dddd, J=15, 8.4, 6.5, 6.5 Hz, 2-H), 2.83(1H, ddd, J=15.8, 8.4, 4.8 Hz, 3-H), 3.12(1H, ddd, J=15, 7.2, 8.4, 3-H), 4.21(2H, q, J=2.3 Hz, OCH₂), 5.14(1H, dd, J=6.5, 3.7 Hz, 1-H), 7.23(1H, m), 7.28(2H, m), 7.45(1H, d, J=7 Hz). | 3.52(C≡C—CH₃), 30.11 (C-2), 32.25(C-3), 56.14(OCH₂), 75.45 (C≡C—CH₃), 81.68(C-1), 82.15(C≡C—CH₃), 124.80, 125.16(C-5,6), 126.11, 128.36(C-4,7), 142.10, 144.14(C-3a,7a). | |
| 4.16 510 | 2-[(2-Butynyloxy)-methyl]-1,4-benzodioxane | oil | 2996, 2921, 2858, 2222, 1594, 1492, 1466, 1269, 1097, 1043 | 1.87(3H, t, J=2.4 Hz, 3.70 and 3.80(2H, ABX, J_{AB}=10.1 Hz, J_{AX}=J_{BX}=5.0 Hz, CH—CH₂—O), 4.08(1H, dd, J=7.6, 11.8 Hz, H-3β), 4.20(2H, d, J=2.3 Hz, O—CH₂—C≡), 4.28–4.41(2H, m, H-3α, H-2α), 6.81–6.92(4H, m, C₆H₄) | 3.57(H₃C—C≡), 59.43 (O—CH₂—C≡), 65.58 (CH—CH₂—O), 68.12 (C-3), 71.96(C-2), 74.54 (CH₂—C≡), 83.22 (H₃C—C≡), 117.12, 117.40 (C-5 and C-8), 121.37, 121.56(C-6 and C-7), 143.07, 143.21(C-4a, C-8a) | |
| 4.17 539 | 2-(2-butynyloxy-methyl)-2,3-dihydro-benzofuran | oil | 3598, 3478 (broad), 3080, 3040, 2996, 2952, 2871, 1611, 1598, 1481, 1462, 1232, 1092, 1050, 1012, 1004, 954, 899, 865 | 2.65(1H, t, J=5.4 Hz, OH), 2.97 and 3.25 (summa 2H, ABX, J_{AB}=15.6 Hz, J_{AX}=9.4 Hz, J_{BX}=7.5 Hz, H-3), 3.79(2H, m, CH₂—OH), 4.90(1H, m, H-2), 6.79 (1H, d, J=8.0 Hz), 6.87 (1H, td, J=7.5, 0.8 Hz), 7.11(1H, d, J=7.8 Hz), 7.16(td, J=7.2, 0.5 Hz) | 31.18(C-3), 64.77 (CH₂—OH), 83.02 (C-2), 109.36(C-7), 120.54(C-5), 124.97 (C-6), 126.48(C-3a), 127.95(C-4), 159.08 (C-7a) | |
| 4.18 330 | S-(−)-1-[1-(2-butynyloxy)-ethyl]-naphthalene | oil | like 4.2 292 | | | (−) 78° (c=1, MeOH) |
| 419 331 | R-(+)-1-[1-(2-butynyloxy)-ethyl]-naphthalene | oil | like 4.2 292 | | | (+) 155° (c=1, chloroform) |
| 4.20 456 | S-(−)-2-[1-(2-butynyloxy)-ethyl]-naphthalene | oil | like 4.7 293 | | | (−) 190.8° (c=1.0, chloroform) |
| 4.21 | R-(+)-2-[1-(2- | oil | like 4.7 293 | | | (+) 199.0° |

-continued

| | Compound | Mp (C. °) | IR ν(cm$^{-1}$) | 1H-NMR δ (ppm) | 13C-NMR δ (ppm) | $[\alpha]_D^{20}$ |
|---|---|---|---|---|---|---|
| 455 | butynyloxy)-ethyl]-naphthalene | | | | | (c=1.17, chloroform) |
| 4.22 474 | S-(-)-2-[1-(2-propynyloxy)-ethyl]-naphthalene | oil | like 4.6 256 | | | (−) 224.4° (c=1.18, chloroform) |
| 4.23 475 | R-(+)-2-1[1-(2-propynyloxy)-ethyl]-naphthalene | 28–29 | like 4.6 256 | | | (+) 228° (c=1, chloroform) |

5. Aromatic Alkyl-alkyl-alkynyl-amine Derivatives

General Procedure

The amine was dissolved in dry benzene, the alkynyl bromide was added and the mixture was stirred at room temperature. Then it was diluted with water and ether, the phases were separated, the aqueous phase was twice extracted with ether, the combined organic phases were washed with water, and dried on MgSO$_4$.

Work-up: the precipitated Ph$_3$PO was filtered off, the filtrate was washed with water dried and evaporated. The residue was chromatographed.

C.)

0.01 mol of phenol were dissolved in 7 ml of dry acetonitrile and under argon atmosphere it was cooled to −4° C. To the solution were then added 1.968 g (0.0129 mol) DBU, keeping the temperature below −4° C. To the resulting

| | Compound | Mp (C.°) | IR ν (cm$^{-1}$) | 1H-NMR δ (ppm) | 13C-NMR δ (ppm) |
|---|---|---|---|---|---|
| 5.1 251 | N-α-dimethyl-N-2-propynyl-β-naphthyl-methylamine | 51–53 | 3173, 3053, 2970, 2941, 2837, 2788, 1600, 1444, 1433, 1371, 1334, 1295, 1227, 1123, 1074, 1011, 969, 952, 935, 900, 863, 827, 754, 734, 713, 557, 482 | 1.455 (3H, d, CH—Me), 2.271 (1H, s, CCH), 2.360 (3H, s, NMe), 3.253–3.302 and 3.487–3.530 (2H, CH2), 3.708–3.757 (1H, m, CHMe), 7.260–7.834 (7H, m, aromatic) | |

6. Aryl Alkynyl Ethers

General Procedure

A.)

The appropriate phenol was dissolved in dry DMF and to the solution dry K$_2$CO$_3$ and the appropriate alkynyl halogenide were added. The reaction mixture was heated to 60° C. and stirred at that temperature for 3–6 hours. DMF was then distilled off in vacuo, the residue was taken up in the mixture of chloroform and distilled water. The phases were separated, the aqueous phase was twice extracted with chloroform, the combined organic phases were washed consecutively with water and saturated sodium chloride solution, dried on MgSO$_4$ and evaporated. The raw product was purified by chromatography.

B.)

Ph$_3$P was dissolved in dry benzene in an inert atmosphere and to the solution the appropriate alcohol and then the phenol were added. The mixture was cooled to 0–10° C., and DEAD (diethyl-azo-dicarboxylate) was added slowly, in small portions, keeping the temperature below 10° C. The reaction mixture was stirred for 10–24 hours.

solution 1.8 g copper(II)-chloride were added and paralelly the trifluoroacetate of the other reactant was prepared.

0.0115 mol alkynyl-alcohol were dissolved in 7 ml of acetonitrile, and the solution was cooled to −5° C., under argon atmosphere. To the solution were added 1.968 g (0.0129 mol) DBU, while keeping the temperature below −5° C. To the mixture were added dropwise 1.6 g (0.011 mol) trifluoroacetic anhydride, keeping the temperature below 2° C. The resulting mixture was stirred at 0° C. for 30 mins.

The trifluoroacetate solution thus obtained was added dropwise to the first solution, keeping the temperature below 0° C. and the mixture was srirred at 0° C. for 5 hours. The reaction was followed by TLC. At the end of the reaction the acetonitrile was distilled off in vacuo. The residue was shaken with the mixture of 150 ml of benzene and 50 ml of water. The organic layer was washed consecutively with 1N hydrochloric acid, 1N sodium hydroxide, water and saturated sodium chloride solution, then dried and evaporated. The product was purified by chromatography.

|  | Compound | Mp (C.°) | IR ν (cm⁻¹) | 1H-NMR δ (ppm) | 13C-NMR δ (ppm) |
|---|---|---|---|---|---|
| 6.1 547 | 1-(3-butynyloxy)-4-nitro-benzene | 92–94 | 3287, 3111, 3085, 3075, 2964, 2947, 2920, 1609, 1596, 1510, 1466, 1344, 1333, 1263, 1179, 1110, 1019, 856, 846, 753, 669, 653. | 2.07 (1H, t, J=2.6 Hz, C≡C—H), 2.73 (2H, td, J=6.8, 2.6 Hz, $CH_2C≡C$), 4.18 (2H, t, J=6.8 Hz, $OCH_2$), 6.97 and 8.18 (summa 4H, dm, J=9 Hz, $C_6H_4$) | 19.37 (C≡C—$CH_2$), 66.60 (C≡CH), 70.38 ($OCH_2$), 79.62 (C≡CH), 114.51 (C-2, C-6), 125.89 (C-3, C-5), 141.73 (C-4), 163.40 (C-1) |
| 6.2 540 | 1-(3-pentynyloxy)-4-nitro-benzene | 77–78 | 3067, 3048, 2963, 2917, 2886, 1923, 1607, 1594, 1512, 1467, 1403, 1339, 1260, 1178, 1110, 866, 856, 753, 694, 648, 628, 522, 506. | 1.78 (3H, t, J=2.3 Hz, C≡C—$CH_3$), 2.66 (2H, m, $CH_2C≡C$), 4.12 (2H, t, J=7.0 Hz, $OCH_2$), 6.95 and 8.18 (summa 4H, dm, J=9 Hz, $C_6H_4$) | 3.57 (C≡C—$CH_3$), 19.61 (C≡C—$CH_2$), 67.26 ($OCH_2$), 74.27 (C≡C—$CH_3$), 77.84 (C≡C—$CH_3$), 114.49 (C-2, C-6), 125.85 (C-3, C-5), 141.59 (C-4), 163.59 (C-1). |
| 6.3 377 | 2,3-dihydro, 2,2-dimethyl-7-(3-butynyloxy)-benzofuran | 78–80 | 3277, 3071, 3043, 2970, 2923, 2889, 2858, 2119, 2022, 1874, 1795, 1714, 1656, 1624, 1611, 1591, 1492, 1470, 1440, 1492, 1396, 1385, 1371, 1302, 1283, 1244, 1201, 1172, 1128, 1077, 999, 972, 946, 887, 838, 780, 753, 720, 682, 663, 635, 600, 546, 502, 458 | 1.512 (6H, s, diMe), 2.033 (1H, t, CH), 2.710 (2H, m, —CH2C), 3.027 (2H, s, CH2-ar), 4.206 (2H, t, O—CH2), 6.739–6.815 (3H, m, aromatic) | 19.12 (CH2—C), 27.88 (diMe), 42.93 (C-3), 66.79 (C-2), 69.961 (O—CH2), 79.96 (CCH), 87.06 (CC), 113.31 (C-6), 117.86 (C-5), 119.99 (C-4), 128.36 (C-9), 142.62 (C-7), 147.52 (C-8) |
| 6.4 418 | 2,3-dihydro-2,2-dimethyl-7-(3-pentynyloxy)-benzofuran | 58–59.5 | 2977, 2963, 2942, 2918, 2880, 2849, 1621, 1591, 1492, 1468, 1389, 1369, 1329, 1305, 1286, 1245, 1203, 1174, 1135, 1115, 1080, 1065, 966, 947, 881, 860, 841, 779, 751, 718, 634, 598, 532, 499. | 1.510 (6H, s, diMe), 1.800 (3H, t, Me), 2.627–2.672 (2H, m, —CH2C), 3.023 (2H, s, CH2-ar), 4.150 (2H, t, O—CH2), 6.751–6.784 (3H, m, aromatic) | 3.471 (Me), 19.63 (CH2—C), 28.18 (diMe), 43.26 (C-3), 67.54 (C-2), 74.82 (CC—Me), 77.32 (O—CH2), 87.26 (CC), 113.21 (C-6), 117.87 (C-5), 120.25 (C-4), 128.48 (C-9), 143.12 (C-7), 145.00 (C-8) |

7. Alkynyl-oxim-ethers

General Procedure

The oxime was transformed to the oxim-ether in the classical way, by reacting it with the alkynyl bromide in dimethyl formamide in the presence of potassium carbonate (See method A under the preparation of naphthyl ethers). The raw product was in each case purified by column chromatography.

|  | Compound | Mp (C.°) | IR ν (cm⁻¹) | 1H-NMR δ (ppm) | 13C-NMR δ (ppm) |
|---|---|---|---|---|---|
| 7.1 571 | 1-Aceto-naphthon-oxim-(2-butynyl)-ether | oil | 2990, 2919, 2853, 2230, 1604, 1591, 1459, 1436, 1363, 1353, 1309, 1252, 1034, 1017, 1002, 912 | 1.94 (3H, t, J=2.3 Hz, $CH_3$—C≡), 2.41 (3H, s, $CH_3$—C=N), 4.84 (2H, q, J=2.3 Hz, O—$CH_2$), 7.46–7.57 (4H, m), 7.87 (2H, m), 8.15 (1H, m) | 3.80 ($CH_3$—C≡), 17.51 ($CH_3$—C=N), 62.25 (O—$CH_2$), 75.33 ($CH_2$—C≡), 82.75 ($CH_3$—C≡), 125.15, 125.46 (C-6, C-7), 125.96 (C-3), 126.01 (C-3), 126.49 (C-2), 128.40 (C-5), 129.10 (C-4), 130.85 (C-1), 133.86 (C-4a), 135.27 (C-8a), 157.41 ($CH_3$—C=N) |
| 7.2 572 | 3,4-Dimethoxy-acetophenonoxym-(2-butynyl)-ether | 85 | 3080, 3003, 2963, 2929, 2869, 2840, 2237, 1595, 1577, 1518, 1447, 1417, 1337, 1311, 1278, 1249, 1234, 1176, 1153, 1030, 937, 879, 804, 768, 634 621 | 1.87 (3H, t, J=2.3 Hz, $CH_3$—C≡), 2.23 (3H, s, $CH_3$—C=N), 3.88 and 3.90 ($CH_3$O), 4.75 (2H, q, J=2.3 Hz, O—$CH_2$), 6.83 (1H, d, J=8.4, 2 7.15 (1H, dd, J=8.4, 2 Hz), 7.29 (1H, d, J=2 Hz) | 3.77 ($CH_3$—C≡), 12.76 ($CH_3$—C=N), 55.86 ($CH_3$O), 62.23 (O—$CH_2$), 75.27 ($CH_2$—C≡), 82.53 ($CH_3$—C≡), 108.8 (C-5), 110.51 (C-2), 119.28 (C-6), 129.18 (C-1), 148.78 (C-3), 150.14 (C-4), 155.0 ($CH_3$—C=N) |

Activity Results:

EXAMPLE 1

Investigation of Synergistic Activity on House Fly (*Musca domestica*) Following Topical Application In two parallel experiments 10 female. 2–4 day old house flies were treated on the vental side of their thorax with 0.2 μl of the test solution, with the help of Hamilton MicroLab P microdispenser. Beside fixed synergist dose of 1000 ng/fly the animals were treated with carbofuran at a dose of 20 ng/fly. For solvent cellosolve was used. Selection and counting of the flies were performed under the action of $CO_2$. After treatment the flies were kept in plastic cups covered with tulle. Mortality after 24 hours was expressed in %. Results are demonstrated in the table below:

| Material | Carbofuran + synergist (ng/fly) | |
|---|---|---|
| | 20 + 0 | 20 + 1000 |
| | mortality % | |
| Alkynyl ester, amides, imides | | |
| 501 | 3 | 53 |
| 502 | 0 | 47 |
| 523 | 0 | 17 |
| 535 | 3 | 27 |
| 541 | 0 | 46 |
| 542 | 0 | 42 |
| Aryl- alkyl- alkynyl ethers | | |
| 279 | 0 | 72 |
| 256 | 0 | 32 |
| 441 | 1 | 97 |
| 484 | 0 | 63 |
| 493 | 1 | 100 |
| 599 | 10 | 100 |
| 503 | 0 | 95 |
| 292 | 0 | 72 |
| 293 | 0 | 45 |
| 454 | 0 | 75 |
| 472 | 1 | 68 |
| 479 | 1 | 58 |
| 330 | 0 | 62 |
| 331 | 0 | 72 |
| 455 | 0 | 70 |
| 456 | 0 | 47 |
| 389 | 2 | 27 |
| 554 | 0 | 58 |
| 555 | 0 | 90 |
| 539 | 0 | 48 |
| 474 | 0 | 50 |
| 510 | 2 | 75 |
| 498 | 5 | 70 |
| 475 | 0 | 47 |
| Aromatic alkyl- alkyl-alkynyil- amine derivatives | | |
| 251 | 2 | 37 |
| Aryl alkynyl ethers | | |
| 547 | 0 | 47 |
| 540 | 0 | 60 |
| 377 | 0 | 57 |
| 418 | 0 | 63 |
| Aralkyl-aldoxime, ketoxime-alkynyl ethers | | |
| 571 | 0 | 53 |
| 572 | 0 | 55 |

EXAMPLE 2

Investigation of Synergistic Activity on Cotton Bollworm (*Helicoverpa armigera*) Following Topical Application Treatment was performed similarity as described in Example 1. but L2 stadium grubs of cotton bollworms (*Helicoverpa armigera*) were treated as test animals. From the 24 hour dose—mortality data the $LD_{50}$ (ng/grub) values were determined using probit analysis. None of the synergists acted at the applied 1000 ng/grub dose. Synergist ratio was calculated as the quotient of the $LD_{50}$ values of carbofuran administered alone, and with the synergist. The experiments were performed in 2–4 replica. Synergist ratios are demonstrated in the table below:

| Materials | Synergist ratio |
|---|---|
| Alkynyl-esters, amides | >5 |
| 501, 502, 523, 535, 541, 542, 537 | |
| Aryl-alkyl alkyl-alkynyl ethers | >5 |
| 279, 256, 441, 484, 493, 503, 292, 293, 454, 510, 475, 498, 479, 472, 331, 455, 456, 389, 554, 555, 539, 474, 330, 599 | |
| Aromatic alkyl- alkyl-alkynyl-amine derivatives | >5 |
| 251 | |
| Ayil alkynyl ethers | >5 |
| 540, 377, 418 | |
| Alkynyl-oximethers | >5 |
| 571 | |
| 572 | |

EXAMPLE 3

Investigation of Synergist Spectrum on House Fly (*Musca domestica*) and Cotton Bollworm (*Helicoverpa armigera*) Following Topical Administration Synerzistic activities of materials No. 279 and 599 of the present invention for various active ingredients were determined on house fly (*Musca domestica*) and cotton bollworm (*Helicoverpa armigera*) using methods of treatments as described in biological Examples 1 and 2. For the active ingredients ISO common names are given (see: Pesticide Manual 1994). The obtained synergist ratios are shown below:

| | 279 | | 599 | |
|---|---|---|---|---|
| active ingredient | Musca domestica | Helicoverpa armigera | Musca domestica | Helicoverpa armigera |
| | Synergist ratio | | Synergist ratio | |
| CARBOFURAN ® | >20 | >10 | >20 | >20 |
| BENDIOCARB ® | >20 | >10 | >40 | >20 |
| ISOPROCARB ® | >40 | — | >40 | >20 |
| FENOBUCARB ® | >10 | — | >20 | — |
| AMINOCARB ® | >20 | — | >20 | — |
| THIODICARB ® | >10 | — | >10 | — |
| METHOMYL ® | >10 | — | >10 | — |
| PIRIMICARB | >20 | — | >20 | — |
| DIOXACARB ® | >20 | — | >40 | >20 |
| PROPOXUR ® | >20 | >10 | >40 | >20 |
| IMIDACLOPRID ® | >5 | — | >5 | — |
| LINDAN ® | >5 | >5 | — | — |
| AZINPHOSMETHYL ® | >5 | >5 | — | — |
| CHLORPYRIPHOS ® | >5 | >5 | — | — |
| ESBIOL ® | >5 | — | >10 | — |
| PERMETHRIN ® | | | >5 | >10 |
| TETRAMETHRIN ® | | | >5 | — |

EXAMPLE 4

Effect of the Active Ingredient:Synergist Ratio on the Synergistic Activity

Treatment was performed as described in Example 1. using Hamilton MicroLab P microdispenser. In two parallel experiments 10 female –3 day old flies were treated on the ventral side of their thorax with 0.2 $\mu$l test solution. Beside 1000–400–200–80 ng/fly fixed doses of the synergist they were treated with constant 20 ng/fly CARBOFURAN®. Selection and counting of the flies were performed under the action of $CO_2$. After treatment the flies were kept in plastic cups covered with tulle. After 24 hours mortality % was recorded. Depending on the results the experiments were performed in 2–4 replica. Results are demonstrated in the table below.

| | Dose of the Synergist (ng/fly) | | | | |
|---|---|---|---|---|---|
| | 0 | 80 | 200 | 400 | 1000 |
| Materials | 24 hour mortality (%) | | | | |
| 501 | 0 | 60 | 75 | 80 | 80 |
| 441 | 0 | 62 | 67 | 90 | 95 |
| 493 | 0 | 75 | 88 | 94 | 100 |
| 503 | 0 | 37 | 50 | 65 | 93 |
| 454 | 0 | 40 | 45 | 60 | 75 |
| 455 | 0 | 25 | 48 | 63 | 77 |
| 599 | 0 | 65 | 90 | 95 | 100 |

EXAMPLE 5

Investigation of Synergistic Activity on Resistant House Fly (*Musca domestica*) Populations The table below demonstrates synergistic activities of materials of the present invention for various active ingredients on two resistent house fly strains (INSEL, IX). Investigation was carried out as described in biological Example 1. $LD_{50}$ values and synergist ratios were determined as given in Example 2.

| | INSEL strain | | IX strain | |
|---|---|---|---|---|
| Treatment | LD50 (ng/fly) | SR | LD50 (ng/fly) | SR |
| CARBOFURAN ® | 15375 | | >100000 | |
| +279 | 29 | 530 | 94 | 4760 |
| METHOMYL | 475 | | 851 | |
| +279 | 46 | 10 | 109 | 5 |
| PIRIMICARB ® | >100000 | | >100000 | |
| +279 | 696 | 145 | 3562 | 115 |
| ALDICARB ® | 695 | | 2104 | |
| +279 | 172 | 4 | 507 | 4 |
| BENDIOCARB ® | 100000 | | 100000 | |
| +279 | 150 | 667 | 746 | 134 |
| ISOPROCARB ® | >100000 | | >100000 | |
| +279 | 983 | 102 | 2145 | 47 |
| ESBIOL ® | 10653 | | — | |
| +279 | 794 | 13 | — | — |

EXAMPLE 6

Investigation of Synergistic Activity on Oat Aphid (*Rhopalosiphum padi*)

5–8 cm high oat plants, sawn in plastic cups were infected with different aged specimens of Rhopalosiphum padi aphids The settled aphids were counted before the treatment, then the plants were sprayed using a hand sprayer, with 1 ml of the spray solution, beside the administration of fixed dose (30 ppm) of the synergist. Of compound No. 279 of the present invention a 100 g/l concentration emulgeable concentrate was prepared by methods usual in the formulation praxis, applying solvent and surface active materials. Test solutions used for the spraying were prepared from this concentrate and from marketed preparations bv dilution. Mortality of the aphids was determined 24 hours after the treatment. Results are shown below:

EXAMPLE 7

Investigation of the Effect on Fecundity, on House Fly (*Musca domestica*)

Groups consisting of freshly hatched 50 male and 50 female flies were fed during 48 hours with granulated sugar comprising 500 ppm of material No. 441 and 484 of the present invention respectively, and the eggs layed on the next 10 days were raised. The fecundity-hindering effect was expressed as the quotient of the emerged flies in the treated and untreated groups. The experiments were performed in 4 replica.

| Treatment | Hindering effect on fecundity |
|---|---|
| 441 | 87% |
| 484 | 90% |

EXAMPLE 8
Synergism of Acaricidal Effect Investigated on Two-spotted Spider Mite (*Tetranychus urticae*)

From the first pair of leaves of a 1 week old bean plant leaf-discs of 225 mm diameter were cut which were treated by dipping them (5 min) into the test solution consisting of the active ingredient and the synergist in definite concentrations. For the preparation of the stock solutions of required concentration, 10% acetone as co-solvent and 0.1% Tween-80 as detergent were applied. The dried leaf-discs were placed on wet surface and they were infected with 10 grown-up female mites per leaf. After 48 hours the mortality was recorded using microscope and a brush. The experiment was performed in 4 replica. Averages of the results are shown in the table below.

| Treatment with the active ingredients alone | Concentration (ppm) | | | | |
|---|---|---|---|---|---|
|  | 31 | 62 | 125 | 250 | 500 |
|  |  |  | Mortality % |  |  |
| 279 | 0 | 6 | 8 | 18 | 30 |
| CARBOFURAN ® | 13 | 39 | 44 | 81 | 90 |
| BROMOROPYLATE ® | 18 | 28 | 90 | — | — |

| Treatment with the active ingredients in combinations | Concentration (ppm) | | | | |
|---|---|---|---|---|---|
|  | 16 + 16 | 31 + 31 | 62 + 62 | 125 + 125 | 250 + 250 |
|  |  |  | Mortality (%) |  |  |
| 279 + CARBOFURAN ® | 29 | 80 | 80 | 100 | 100 |
| 279 + BROMOPROPYLATE ® | 75 | 90 | 100 | — | — |

EXAMPLE 9
Efficacy in Field Trial Against Colorado Potato Beetle (*Leptinotarsa decemlineata*)

Of compound No. 279 of the present invention a 100 g/l concentration emulgeable concentrate was prepared by methods usual in the formulation praxis, applying solvent and surface active materials. CHINUFUR 40 FW composition, comprising 400 g/l carbofuran was applied together with a fixed dose of 2 l/ha of compound No. 279, in a small plot field study against Colorado potato beetle (Leptinotarsa decemlineata). Spraying was carried out with motoric sprayer (Maruyama) applying 300 I/ha spray solution. Treatments were performed in 4 replica, on plots of 25 m2. The effect of the treatments was evaluated on the 2nd day by counting the surviving beetles on the plants. Results are shown in the table below:

| Treatment | Dose (l/acre) | carbofuran: 279 ratio | Number of potato beetles piece/plant | |
|---|---|---|---|---|
|  |  |  | before treatment | after treatment |
| untreated, | — | — | 23.6 | 28.0 |
| CHINUFUR ® 40 FW, | 0.1 | 1:0 | 18.4 | 6.1 |
| CHINUFUR ® 40 FW, | 0.2 | 1:0 | 32.0 | 6.8 |
| CHINUFUR ® 40 FW, + 279 | 0.1 + 2.0 | 1:5 | 21.3 | 0.4 |

EXAMPLE 10
Synergist Activity of Compound Nr. 599

Synergist activity of compound 599 with various specific acaricides was investigated against two-spotted spider mite (Tetranychus urticae), by the method described in Example 8. The $LC_{50}$ and $LC_{95}$ values calculated from the concentration-mortality relationship are shown in the table below.

Synergist Activity Against Two-spotted Spider Mite (*Tetranychus urticae*)

| Treatment | Ratio of Acaricide/ Synergist | Exposure time (h) | $LC_{50}$ (mg/l) | $LD_{95}$ (mg/l) | Synerg ratio | |
|---|---|---|---|---|---|---|
|  |  |  |  |  | $SR_{50}$ | $SR_{95}$ |
| CARBOFURAN ® | 1:0 | 24 | 163.9 | 799.9 | — | — |
| CARBOFURAN ® + MB-599 | 1:1 | 24 | 55.5 | 286.8 | 3.0 | 2.8 |
|  | 1:2 | 24 | 33.5 | 93.7 | 4.9 | 8.5 |
|  | 1:4 | 24 | 27.5 | 67.0 | 6.0 | 11.9 |
| FENAZAQUIN ® | 1:0 | 3 | >1000 | — | — | — |

-continued

| Treatment | Ratio of Acaricide/ Synergist | Exposure time (h) | LC$_{50}$ (mg/l) | LD$_{95}$ (mg/l) | Synerg ratio SR$_{50}$ | SR$_{95}$ |
|---|---|---|---|---|---|---|
|  | 1:0 | 24 | 41.9 | 801.3 | — | — |
| FENAZAQUIN ® + PBO | 1:1 | 3 | 326.7 | >1000 | >3.1 | — |
|  | 1:1 | 24 | 20.4 | 371.8 | 2.1 | 2.2 |
| FENAZAQUIN ® + MB-599 | 1:1 | 3 | 68.1 | 280.2 | >15 | — |
|  | 1:1 | 24 | 31.3 | 174.8 | 1.3 | 4.6 |
| TEBUFENPYRAD ® | 1:0 | 3 | >1000 | — | — | — |
|  | 1:0 | 24 | 63.4 | >1000 | — | — |
| TEBUFENPYRAD ® + PBO | 1:1 | 3 | 115.9 | 1081 | >9 | — |
|  | 1:1 | 24 | 35.7 | 118.0 | 1.8 | >8.5 |
| TEBUFENPYRAD ® + MB599 | 1:1 | 3 | 61.8 | 658.7 | >16 | — |
|  | 1:1 | 24 | 22.3 | 141.8 | 2.8 | >7.0 |

EXAMPLE 11
Synergist Activity Against Pea Aphid (*Acyrthosiphon pisun*)

Synergist activity of compound No. 599 was tested against pea aphid (Acyrthosiphon pisun) in field trials on small plots (10 m$^2$). 300 l/ha spray volume was applied using motoric sprayer (Maruyama). Efficacy was expressed by the average number of aphids/leaf before, and two days after the treatment, respectively. (Henderson and Tilton: J. Econ. Entomol., 48:157, 1955). Results are shown in the table below.

| Treatment | Dose act. ingr./ha. | E (%) |
|---|---|---|
| PIRIMICARB ® | 250 | 93.8 |
|  | 80 | 86.3 |
| PIRIMICARB ® + MB-599 | 80 + 80 | 95.5 |
| FIPRONIL ® | 240 | 94.6 |
| FIPRONIL ® + MB-599 | 120 + 120 | 95.7 |
| CARBOFURAN ® | 160 | 99.1 |
|  | 110 | 98.0 |
| CARBOFURAN ® + MB-599 | 110 + 110 | 100.0 |
| TRIAZAMATE ® | 50 | 96.8 |
| TRIAZAMATE ® + MB-599 | 33 + 33 | 97.7 |
| IMIDACLOPRID ® | 120 | 98.4 |
| IMIDACLOPRID ® + MB-599 | 120 + 120 | 100.0 |

EXAMPLE 12
Comparative Investigations with Known Reference Synergists

LD$_{50}$ values of the reference compounds were determined in 4 replica on flies treated with carbofuran and 1000 ng of the known synergist, and the SR$_{50}$ ratios were counted in relation to the control carbofuran. These SR$_{50}$ ratios were compared to those of the new compounds prepared by us. Our compounds were more active in each case.

|  |  | known | according to the invention |
|---|---|---|---|
| 1. Alkynyl esters |  |  |  |
| Synergist ratio | 2-propynyll-naphthyl-carboxylate |  | 502 |
| SR$_{50}$ | 4.11 |  | 6.28 |
| 2. (Aryl-alkyl), alkyl-alkynyl ethers |  |  |  |
| Synergist ratio | (2,6-dichlorophenyl)methyl 2-propynyl ether |  | 503 |
| SR$_{50}$ | 20.92 |  | 21.16 |
| Synergist ratio | 5-[(2-propynyl)-methyl]-1,3-benzodioxole |  | 441 |
| SR$_{50}$ | 10.60 |  | 25.70 |
| Synergist ratio | 1-naphthylmethyl 2-propynyl ether |  | 279 |
| SR$_{50}$ | 5.28 |  | 28.7 |
| Synergist ratio | 2-[(2-propynyloxy)methyl]-1,4-benzodioxane |  | 510 |
| SR$_{50}$ | 5.58 |  | 18.32 |
| Synergist ratio | (2-propynyloxy-methyl)-3,4-dimethoxy-benzene |  | 493 |
| SR$_{50}$ | 6.58 |  | 32.84 |
| 3. Aryl alkynyl ethers |  |  |  |
| Synergist ratio | 2,3-dihydro-2,2-dimethyl-7-(2-propynyloxy)benzofurane |  | 418 |
| SR$_{50}$ | 1.8 |  | 20.5 |

| Known naphthyl alkynyl ether | Synergist ratio SR$_{50}$ |
|---|---|
| 1-naphthyl 2-propargyl ether | 6.52 |
| 1-naphthyl 3-butynyl ether | 7.95 |
| 2-naphthyl 2-butynyl ether | 7.72 |
| 2-naphthyl 3-pentynyl ether | 9.97 |

|  |  | known | according to the invention |
|---|---|---|---|
| 4. Alkynyl-oxim-ethers |  |  |  |
| Synergist ratio | 1-acetonaphthon-oxim (2-propynyl) ether |  | 571 |
| SR$_{50}$ | 7.79 |  | 10.02 |

EXAMPLES FOR FORMULATION

Names of the marketed auxiliary materials are given in quotation marks, followed by the makers name.

1. Preparation of Powders

A)

To 158 g of fine-grained perlite 20 g of carbofuran and 20 g of compound 279, were mixed in a homogenizator to this mixture were added 2 g of fatty alcohol polyglycol ether ("G-3920" ICI) and the mixture was homogenized. The powder mixture was grained in an ejector mill and to it were added 5 g of octyl-phenol-polyglycol-ether (EO=20) ("Triton X-165" Rohm & Haas) and 2 g of alkyl-sulfosuccinate ("Aerosol-13" Cyanamid). The resulting product is a wettable powder mixture (WP).

B)

10 g of compound 279 and 10 g of carbofuran were diluted with 2 g of ethanol. The solution was mixed in a powder homogenisator with 5 g of calcium-lignin-sulfonate ("Borrespeseca" Borregard), 5 g of nonyl-phenolpolyglycol-ether (EO=20) ("Arkopal N-200" Hoechst), and 70 g of calcium carbonate. The resulting product was grained in an alpine-100 typ mill. Average particle size was 1–2 μm. This composition may be used to prepare microsuspensions.

C)

The mixture of 3 g of Diazinon. 3 g of compound 441. and 0.3 g of fatty alcohol-polyglycol-ether ("G-3920" ICI) was taken up in a homogenisator apparatus on the mixture of 1.0 g synthetic silicic acid (Aerosil 200) and 191 g talc ($d_{max.}$=15–30 μm), the pH of the latter was previously adjusted to pH=7.0 with potassium- and sodium-phosphate buffer. Under further stirring 1 g of dioctyl-sulfo-succinate ("AEROSOL OTB®" CYANAMID) and 1 g of fatty alcohol-polyglycol-ether-sulfonate ("GENAPOL LRD®" HOECHST) were added and finally the mixture was grained to an average particle size of 20 μm. The resulting product is an easy flowing powder preparation.

2. Preparation of Emulsion Concentrates

A)

The mixture of 5 g of pirimicarb and 5 g of compound 493 was dissolved in the mixture of 20 g of xylene and 40 g of propanol. To this solution was added the mixture of 4 g of ethoxylated alkyl-phenol+lineare alkyl-aryl-sulfonate-calcium salt ("GERONOL FF®/U" Geronazzo) and 6 g of ethoxylated amine+fatty acid+lineare alkyl-arylsulfonate alkali metal salt ("GERONOL MS®" GERONAZZO). After complete dissolution 20 g of water were added. Transparent solution was obtained, for which is characteristic, that on dilution with water it forms an emulsion of 0.8–1.5 μm drop-diameter.

B)

The mixture of 5 g of quinalphos and 10 g of compound 484 and the mixture of 7 g of ethoxylated-(EO=13)-propoxylated-(PO=21)-nonylphenol, 2 g of lineare-dodecylbenzenesulfonic acid-calcium salt and 12 g POE-(20)-sorbitan-monooleate were dissolved in the mixture of 28.6–28.6 ml of propyleneglycol and pine-fatty acid and 23.8 ml of sun-flower oil, 9.5 ml of etanol and 95 ml of aliphatic hydrocarbone with 45% naphthene contant. The material thus obtained may be preferably used for the preparation of microemulsions.

C)

The mixture of 0.02–0.02 parts by mass of the active ingredient and of the synergist is dissolved in 10 parts by mass of propanol, to the resulting solution 99.96 parts by mass of odourless petroleum are added and the mixture is stirred until a homogenous solution is obtained. The resulting oily dispersible preparation can directly be used in ULV applications.

D)

The method described in example A) is followed, with the difference that 10 g of compound 279 is applied as synergist active ingredient.

3. Preparation of Granulates

In a mechanical granulator are mixed 300 g of carbofuran, 300 g of compound 418, 1500 g of polycarboxylate alkali salt ("SORPHOL®," TOHO), 500 g of dodecyl-benzenesulfonic acid sodium salt ("MARLON TP 370®" HULS), 500 g of beet sugar and 7200 g of caolinite. The powder mixture thus obtained is mixed with 8300 ml of water using a mixer of high shear force (v=10 m/s). The mixture is finally spray-dried. Particle-size distribution of the product is 0.1–0.4 mm.

4. Preparation of Aerosols

In a 100 l apparatus supplied with stirrer are mixed 1 kg of BIOALLETHRIN®, 0.5 kg of compound 441, 0.1 kg of aerosil-air 972, 0.1 kg of ethyleneglycol-monosalicylate, 15 kg of odorless petroleum and 50 kg of propanol. After dissolution it is filled into cylinders with 33.3 kg of liquid propane-butane (25–75) gas.

5. Preparation of Vaporizers

In 60 ml of ethanol are dissolved 5 g of S-BIOALLETHRIN®, 5 g of compound 279 and 1 g of lemon aroma. The solution is applied in vaporizers, at a temperature of 50° C.

What we claim is:

1. Compounds of the general formula I:

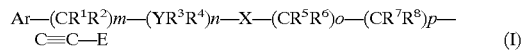

or optically active isomers and salts thereof, wherein

Ar is alicyclic, aromatic or heterocyclic, optionally substituted by one or more alkoxy, methylenedioxy, alkyl, halogen, haloalkyl, or nitro groups and/or condensed with a benzene ring;

$R^1$ and $R^2$ are independently H, alkyl, alkenyl, haloalkyl, phenyl, substituted phenyl or cycloalkyl;

$R^3$ and $R^4$ are independently H, alkyl, alkenyl, haloalkyl, phenyl, substituted phenyl or cycloalkyl, or $R^3$ and $R^4$ are together O;

Y is C or PO, or $YR^3R^4$ is

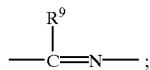

X is O or —$NR^{10}$—;

$R^9$ is H, alkyl, phenyl or substituted phenyl;

$R^{10}$ is H or alkyl;

$R^5$, $R^6$, $R^7$ and $R^8$ are each independently H, alkyl, alkenyl or haloalkyl;

E is H, halogen or methyl;

m=0, 1, 2;

n=0, 1;

o=0, 1, 2; and p=0, 1, 2, with the following provisos:

(1) that the sum of atoms or groups of the bridge —(CR$^1$R$^2$)m—(YR$^3$R$^4$)n—X—(CR$^5$R$^6$)o—(CR$^7$R$^8$)p is 3 and the —C≡C—E skeleton forms a linear chain with the atoms of the bridge, wherein the linear chain is a 6-atom linear chain ending with a methyl group;

(2) if Ar is phthalimide, $R^1$ is methyl, m is 1, n is 0, o is 1, Rs is H, $R^6$ is H and p is 0, then E is not H;

(3) if Ar is naphthyl, m is 0, n is 0, X is O, $R^5$ is H, $R^6$ is H, $R^7$ is H, and $R^8$ is H, then E is not H; and (4) if Ar is substituted or unsubstituted phenyl or naphthyl, m is 0, n is 1, X is O, Y is C, $R^3$ and $R^4$ are each H or $R^3$ and $R^4$ are together O, or $YR^3R^4$ are together $R^9$—C=N, where $R^9$ is H or alkyl, then E is not H.

2. The compound of claim 1, wherein the compound has the general formula IA:

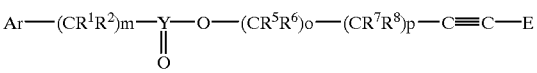

or optically active isomers thereof;

wherein Ar, $R^1$, $R^2$, $R^3$, $R^4$, $R^5$, $R^6$, $R^7$, $R^8$, Y, E, m, o, and p have the same meanings as set forth in claim 1.

3. The compound of claim 1, wherein the compound has the general formula IB:

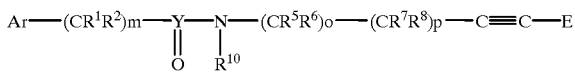

(IB)

or optically active isomers thereof,
wherein Ar, $R^1$, $R^2$, $R^3$, $R^4$, $R^5$, $R^6$, $R^7$, $R^8$, $R^{10}$, E, m, o, and p have the same meanings as set forth in claim 1.

4. The compound of claim 1, wherein the compound has the general formula IC:

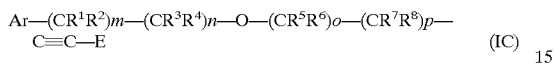

(IC)

or optically active isomers thereof,
wherein Ar, $R^1$, $R^2$, $R^3$, $R^4$, $R^5$, $R^6$, $R^7$, $R^8$, E, m, n, o, and p have the same meanings as set forth in claim 1.

5. The compound of claim 1, wherein the compound has the general formula ID:

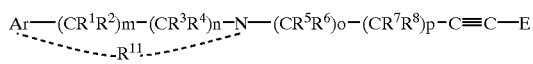

(ID)

or optically active isomers thereof,
wherein $R^{11}$ is a carbonyl group and Ar, $R^1$, $R^2$, $R^3$, $R^4$, $R^5$, $R^6$, $R^7$, $R^8$, E, m, n, o, and p have the same meanings as set forth in claim 1.

6. The compound of claim 1, wherein the compound has the general formula IE:

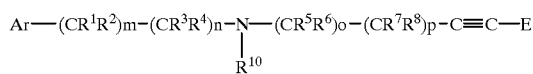

(IE)

or optically active isomers thereof,
wherein Ar, $R^1$, $R^2$, $R^3$, $R^4$, $R^5$, $R^6$, $R^7$, $R^8$, $R^{10}$, E, m, n, o, and p have the same meanings as set forth in claim 1.

7. The compound of claim 1, wherein the compound has the general formula IF:

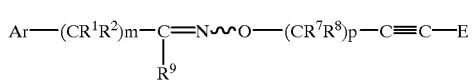

(IF)

or optically active isomers thereof,
wherein Ar, $R^1$, $R^2$, $R^7$, $R^8$, $R^9$, E, m, n, o, and p have the same meanings as set forth in claim 1.

8. A process for preparing a compound of the general formula IA, wherein formula IA is set forth according to claim 2, said process comprising:
reacting compounds of general formulas II and III

 (II)

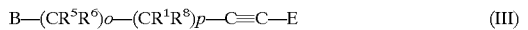 (III)

wherein Ar, $R^1$, $R^2$, $R^5$, $R^6$, $R^7$, $R^8$, E, m, o, and p have the same meanings as set forth in claim 2, and A and B are groups suitable for forming an ester bond.

9. A process for preparing a compound of the general formula IB, wherein formula IB is set forth according to claim 3, said process comprising: reacting compounds of general formulas IV and V

 (IV)

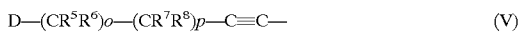 (V)

wherein Ar, $R^1$, $R^2$, $R^5$, $R^6$, $R^7$, $R^8$, E, m, o, and p have the same meanings as set forth in claim 3, and C and D are groups suitable for forming an amide bond.

10. A process for preparing a compound of the general formula IC, wherein formula IC is set forth according to claim 4, said process comprising:
reacting compounds of general formulas VI and VII

 (VI)

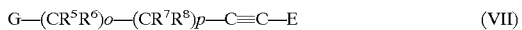 (VII)

wherein Ar, $R^1$, $R^2$, $R^3$, $R^4$, $R^5$, $R^6$, $R^7$, $R^8$, E, m, o, and p have the same meanings as set forth in claim 4, and F and G are groups suitable for forming an ether bond.

11. A process for preparing a compound of the general formula ID, wherein formula ID is set forth according to claim 5, said process comprising:
reacting compounds of general formulas VIII and IX

 (VIII)

 (IX)

wherein Ar, $R^1$, $R^2$, $R^3$, $R^4$, $R^5$, $R^6$, $R^7$, $R^8$, E, m, n, o, and p have the same meanings as set forth in claim 5, and Lg represents a leaving group.

12. A process for preparing a compound of the general formula IE, wherein formula IE is set forth according to claim 6, said process comprising:
reacting compounds of general formulas X and XI

 (X)

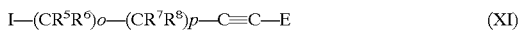 (XI)

wherein Ar, $R^1$, $R^2$, $R^3$, $R^4$, $R^5$, $R^6$, $R^7$, $R^8$, E, m, n, o, and p have the same meanings as set forth in claim 6, and H and I represent groups suitable to form —N—$R^{10}$ where the meaning of $R^{10}$ is the same as set forth in claim 6.

13. A process for preparing a compound of the general formula IF, wherein formula IF is set forth according to claim 7, said process comprising:
reacting compounds of general formulas XII and IX

 (XII)

 (IX)

wherein Ar, $R^1$, $R^2$, $R^5$, $R^6$, $R^7$, $R^8$, E, m, o, and p have the same meanings as set forth in claim 7, Lg represents a leaving group.

14. A pesticide composition comprising an effective amount of a compound according to claim 1 and a carrier therefor, and optionally at least one other active pesticide.

15. An arthropodicide pesticide composition comprising an effective amount of a compound according to claim 1 and a carrier therefor, and optionally at least one other active arthropodicide.

16. The composition according to claim 1, wherein Ar is selected from the group consisting of naphthyl, tetrahydronaphthyl, benzodioxol, benzene, benzofuranyl, tetrahydro-benzofuranyl and indenyl, and Ar is optionally substituted by one or more alkoxy, methylenedioxy, alkyl, halogen, haloalkyl, or nitro groups.

17. The compound according to claim 1, wherein the compound is selected from the group consisting of 1-naphthylmethyl 2-butynyl ether, 2-propynyl-1,3-benzodioxol-5-carboxylate, 1-[(2-butynyloxy)-ethyl]-3,4-dimethoxybenzene, 2,6-dichloro-1-(2-butynyloxy-methyl) benzene, 1-[1-(butynyloxy)propyl]naphthalene, R-(+)-2-[1-(2-butynyloxy)ethyl]naphthalene, 5-[(but-2-ynyloxy) methyl]-1,3-benzodioxole,5-[2-methyl-1-(2-butynyloxy) propyl]-1,3-benzodioxole, 5-[(but-2-ynyloxy) phenylmethyl]-1,3-benzodioxole, 2-[(2-butynyloxy)methyl] 1,4-benzodioxane, and 2,3-dihydro-2,2-dimethyl-7-(3-pentynyloxy)benzofuran.

18. A composition comprising the compound according to claim 1, wherein the composition contains as other active ingredient:

acetamide compounds, benzoylurea compounds, benzoylurea IGR (insect growth regulator) compounds, bicycloheptadiene compounds, cross-bridged diphenyl compounds, carbamates, carbamoyloxime compounds, cyclodienes; diazoles, hydrazides, nereistoxin compounds, nitromidazolidynylenamines, organophosphor compounds, organotin compounds, phenoxy compounds, pyrazoles, pyrethroides, pyridazinones, pyridine compounds, pyrimidine compounds, quinazolines, terpenoid compounds, tetrazines, thiadiazines, thiazolidines, ki azoles, chlorinated hydrocarbons, macrocyclic lactones, tebufenpyrad, fenpyroxymate or triazarnate.

19. The composition according to claim 15 or 18, comprising as general formula I at least one selected from the group consisting of 1-naphthylmethyl 2-butynyl ether, 2-propynyl-1,3-benzodioxol-5-carboxylate, 1-[1-(2-butynyloxy)-ethyl]-3,4-dimethoxybenzene, 2,6-dichloro-1-(2-butynyloxy-methyl)benzene, 1-[1-(butynyloxy)propyl] naphthalene, R-(+)-2-[1-(2-butynyloxy)ethyl]naphthalene, 5-[(but-2-ynyloxy)methyl]-1,3-benzodioxole,5-[2-methyl-1-(2-butynyloxy)propyl]-1,3-benzodioxole, 5-[(but-2-ynyloxy)phenylmethyl]-1,3-benzodioxole, 2-[(2-butynyloxy)methyl]1,4-benzodioxane, and 2,3-dihydro-2,2-dimethyl-7-(3-pentynyloxy)benzofuran.

20. The composition according to claims 1, 14, 15 or 17, further comprising a carbamate suitable for extermination of arthropods.

21. The composition according to claim 20, wherein the carbamate is (2,3-dihydro-2,2-dimethylbenzofuran-7-yl methylcarbamate).

22. The composition according to claim 18, wherein the acetamide compound is (N,N-dimethyl-2-methylcarbamoyloxymino-2-(methylthio)acetamide); the benzoylurea compounds are selected from the group consisting of (1-{α-(4-chloro-α-cyclopropylbenzylideneaminooxy)-p-tolyl}-3-(2,6-difluorobenzoyl)urea), (1-{3,4-dichloro-4-(1,1,2,2-tetrafluoroethoxy)phenyl-3-(2,6-difluorobenzoyl)}urea), (1-(3,5-dichloro-2,4-difluorophenyl)-3-(2,6-difluorobenzoyl) urea) and (1-(2-chlorobenzoyl)-3-(4-trifluoromethoxyphenyl)urea); the bicycloheptadien compound is (7-chlorobicyclo{3.2.0}hepta-2,6-diene-6yl dimethyl phosphate); the cross-bridged diphenyl compounds are selected from the group consisting of (2-(4-ethoxyphenyl)-2-methylpropyl 3-phenoxybenzyl ether), (isopropyl 4,4,dibrombenzilate), (1,1,1-trichloro-2,2-bis(4-methoxyphenyl)ethane), (O,O,O',O'-tetramethyl O,O'-thiodi-p-phenylene diphosphorothioate) and (4-chlorophenyl 2,4,5-tricholorophenyl sulfone); the carbamates are selected from the group consisting of (4-dimethylaminom-tolyl methylcarbamate), (2-methyl-2-(methylthio)propionaldehyde O-methylcarbamoyloxime), (2-methyl-2-methylsulonylpropionldehyde O-methylcarbamoyloxime), (ethyl N-{2,3-dihydro-2,2-dimethylbenzofuran-7-yloxycarbonyl-(methyl)aminothio}-N-isopropyl-β-alanilate), (1-naphthyl methylcarbamate), ((R)-1-(ethylcarbamoyl)ethyl carbanilate), (2,3-dihydro-2,2-dimethylbenzofuran-7-yl methylcarbamate), (2,3-dihydro-2,2-dimethylbenzofuran-7-yl (dibutylaminothio) methylcarbamate), (isopropyl 3,4-diethoxycarbanilate), (2-(1,3-dioxolan-2-yl)phenyl methylcarbamate), (α-ethylthio-o-tolyl methylcarbamate), (2-sec-butylphenyl methylcarbamate), (ethyl 2-(4-phenoxyphenoxy) ethylcarbamate), (butyl 2,3-dihydro-2,2-dimethylbenzofuran-7-yl N,N'-dimethyl-N,N'-thiocarbamate), (2-isopropylphenyl methylcarbamate), (S-methyl N-(methylcarbamoyloxy)thioacetimidate), (N,N-dimethyl-2-methylcarbamoyloxymino-2-(methylthio) acetamide), (2-dimethylamino-5,6-dimethylpyrimidin-4-yl dimethylcarbamate), (2-isopropoxyphenyl methylcarbamate), (dimethyl N,N'-{thiobis{(methylimino) carbonyloxy}}bis(ethanimidothioate)), (3,3-dimethyl-l-methylthiobutanoate O-methylcarbamoyloxime), and (3,3-dimethyl-1-methylthiobutanoate O-methylcarbamoyloxime), the carbamoyloxime compounds are selected from the group consisting of (ethyl (Z)-N-benzyl-N-{{methyl(1-methylthioethylideneamionoxycarbonyl)amino}thio}-β-alanilate) and (3-(methylthio)butanone O-methylcarbamoyloxime); the cyclodienes are selected from the group consisting of ((1R,4S,4aS,5S,8R,8aR)-1,2,3,4,10,10-hexachloro-1,4,4a,5,8,8a-hexahydro-1,4:5,8-dimethanonaphthalene), (1,2,4,5,6,7,8,8-octachloro-2,3,3a,4,7,7a-hexahydro-5,7-methano-1H-indene), and (1,4,5,6,7,8,8-heptachloro-3a,4,7,7a-tetrahydro-4,7-methanoindene), the diazol is ((+)-5-amino-1-(2,6-dichloro-α,α,α-trifluoro-p-tolyl)-4-trifluoromethylsulfinylpyrazole-3-carbonitrile), the hydrazides are selected from the group consisting of (N-tert-butyl-N'-(4-ethylbenzoyl)-3,5-dimethylbenzohydrazide), (N'-benzoyl-N-tert-butyl-benzohydrazide) and ((E)-4,5-dihydro-6-methyl-4-(3-pyridylmethyleneamino)-1,2,4-trianzin-3(2H)-one; the nereistoxin analog is (S,S'-2-dimethylaminotrimethylene di(benzenethiosulfonate)), the nitroimidazolidynylenamines is (1-(6-hloro-3-pyridylmethyl)-N-nitroimidazolidin-2-ylideneamine); the organosulfur compounds are selected from the group consisting of (O,O-diethyl O-quinoxalin-2-yl phosphorothioate), (O,O-diethyl O-2-isopropyl-6-methylpyrimidine-4-yl phosphorothioate), (S-6-chloro-2,3-dihydro-2-oxobenzzoxazol-3-ylmethyl O,O-diethyl phosphorodithioate), (O,O-dimethyl S-methylcarbamoylmethyl phosphorodithioate) and (S-(3,4-dihydro-4-oxobenzo{d}-{1,2,3}-triazin-3-ylmethyl)O,O-dimethyl phosphorodithioate); the organotin compounds are selected from the group consisting of (tri(cyclohexyl)-1H-1,2,4-triazol-1-yltin), (tricyclohexytin hydroxide), (bis{tris (2-methyl-2-phenylpropyl)tin}oxide and (bis{(1-methyl-1-phenyl)ethyl}trimethylsilylmethyltin chloride); the phenoxy compound is (1-tert-butyl-3-(2,6-di-isopropyl-4-phenoxyphenyl)thiourea); the pyrazole is (ethyl 2-diethoxyphosphinothiolyloxy-5-methylpyrozolo{,15-aq}-pyrimidine-6-carboxylate); the pyrethrinoids are selected from the group consisting of (2-methyl-4-oxo-3 (2-propenyl) -2-cyclopenten-1-yl 2,2-dimethyl-3 (2-methyl-1-propenyl)-cyclopropanecarboxylate), ((RS)-³-allyl-2- methyl-4-oxo-cyclopent-2-enyl (1R,3R)-2,2-dimethyl-3(2-methyl-1-propenyl) cyclopropanecarboxylate)), ((S)-3-allyl-2-methyl-4-oxo-cyclonent-2-enyl(1R,3R)-2,2-dimethyl-3-(2-methyl-1-propenyl) cyclopropanecarboxylate), (cyano(3-phenoxyphenyl)methyl 2,2-dimethyl-3-{3-oxo-3-{2,2,2-trifluoro-1-(trifluoromethyl)ethoxy}-1-propenyl}cyclopropanecarboxylate), ((RS)-α-cyano-3-phenoxybenzyl (RS)-2-(4-chlorophenyl)-3-methylbutyrate), ((E)-(RS)-1-ethynyl-2-methylpent-2-enyl(1R,3RS;1R,3SR)-2,2-dimethyl-3-(2-methyl-1-propenyl) cyclopropanecarboxylate), ((S)-2-methyl-4-oxo-3-prop-2-ynylcvclopent-2-enyl(1R)-cis-trans-2,2-dimethyl-3-(2-methyl-1-propenyl)cyclopropanecarboxylate), (5-benzyl-3-furylmethyl (1RS,3RS;1RS,3SR)-2,2-dimethyl-3-(2-methyl-1-propenyl) cyclopropanecarboxylate), (3-{4-(4-ethoxyphenyl)-2-methylpentyl}-6-fluorophenyl phenyl ether), (3-(4-chlorophenoxy)benzyl (RS)-2-(4-ethoxyphenyl)-3,3,3-trifluoropropyl ether), (3-phenoxybenzyl (1RS,3RS;1RS;3SR)-3-(2,2-dichlorovinyl)-2,2-dimethylcyclopropanecarboxylate), (cyclohex-1-ene-1,2-dicarboximinomethyl (1R,3R;1R,3S)-2,2-dimethyl-3-(2-methyl-1-propenyl) cyclopropanecarboxylate), and ((RS)-α-cyano-3-phenoxybenzyl (1RS,3RS;1RS,3SR)-3-(2,2-dichlorovinyl)-2,2-dimethylcyclopropanecarboxylate); the pyridazinone is pyridaben; the pyridine compound is chlorpyriphos; the pyrimidine compounds are pyrimiphos-ethyl or (O,O-dimethyl-O-2-diethylamino-6-methyl-pyrimidine-4-yl phosphorothioate); the pyrrole is (4-bromo-2-(4-chlorophenyl)-1-ethoxymethyl-5-trifluoromethyl-pyrrol-3-carbonitrile); the quinazoline is (4-tert-butylphenethyl quinazolin-4-yl ether); the terpenoid compound is (isopropyl (E,E)-(RS)-11-methoxy-3,7,11-trimethyldodeca-2,4-dienoate, the tetrazine is (3,6-bis(2-chlorophenyl)-1,2,4,5-tetrazine), SzI-121 (3-(2-chlorophenyl)-6-(2,6-difluorophenyl)-1,2,4,5-tetrazine) or; the thiadiazine is (2-tert-butylimino-3-isopropyl-5-phenyl-1,3,5-thiadiazinin-4-one), the thiazolidine is ((4RS,5RS)-5-(4-chlorophenyl)-N-cyclohexyl-4-methyl-2-oxo-4-thiazolidinercarboxamide); the triazole is (O-5-chloro-1-isopropyl-1H-1,2,4-triazol-3-yl O,O-diethyl phosphorothioate) or (ethyl(3-tert-butyl-1-dimethylcarbamoyl-1H-1,2,4-triazol-5-ylthio)acetate); and the chlorinated hydrocarbon is (1,2,3,4,5,6-hexachlorocyclohexane).

23. The composition according to claim 20, wherein the compound of general formula I is 1-(1-(2-butynyloxy)-ethyl)-3,4-dimethoxybenzene.

24. The composition according to claim 20, wherein the compound of general formula I is 5-(but-2-ynyloxy)methyl-1,3-benzodioxole.

25. A method for extermination of pests, comprising treating the pests with an effective amount of the composition of claim 14 or 15 in a tank mixture.

* * * * *

UNITED STATES PATENT AND TRADEMARK OFFICE
CERTIFICATE OF CORRECTION

PATENT NO. : 6,277,867 B1
DATED : August 21, 2001
INVENTOR(S) : Geza Arvai, IIdiko Bakonyvari, Bela Bertok, Laszlo Csiz, Iren Czudor, Zsuzsa R. Kuruczne, Laszlo Pap and Istvan Szekely It is certified that error appears in the above-identified patent and that said Letters Patent is hereby corrected as shown below:

<u>Title page</u>,
ABSTRACT,
Line 2, -- alicyclic -- instead of "alycyclic"

<u>Column 1</u>,
Line 51, -- —C≡C—E -- instead of "—C=C—E"

<u>Column 2</u>,
Line 11, -- -(3-pentynyloxy)benzofuran -- instead of "-(3-pentyloxy)benzofuran"

<u>Column 4</u>,
Line 14, -- Benzaldoxime -- instead of "Benzaidoxime"
Line 19, -- Phenylphosphonic acid propargyl ethers -- instead of "Phenyiphosphonic acid propargyl esters"

<u>Column 6</u>,
Line 9, -- dose/efficacy/cost value -- instead of "doseiefficacyfcost"

<u>Column 11</u>,
Line 39, -- 5 ml/min -- instead of "5 m/min"

<u>Column 12</u>,
Line 15, -- 0-50 °C -- instead of "0-50C"
Line 37, -- triphenylphosphine -- instead of "triphenyiphosphine"

<u>Column 25</u>,
Line 7, -- ventral -- instead of "vental"

<u>Column 26</u>,
Line 9, -- similarly -- instead of "similarity"
Line 54, -- Synergistic -- instead of "Synerzistic"

<u>Column 28</u>,
After line 61, insert following table:

| --Treatment | Mortality % |
|---|---|
| carbofuran 1 ppm | <.50 |
| carbofuran 1 ppm + 279 | >95 |
| pirimor 2 ppm | <30 |
| pirimor 2 ppm + 279 | >95 |
| Imidacloprid 0.1 ppm | <50 |
| Imidacloprid 0.1 ppm - 279 | >95-- |

UNITED STATES PATENT AND TRADEMARK OFFICE
CERTIFICATE OF CORRECTION

PATENT NO. : 6,277,867 B1
DATED : August 21, 2001
INVENTOR(S) : Geza Arvai, IIdiko Bakonyvari, Bela Bertok, Laszio Csiz, Iren Czudor, Zsuzsa R. Kurczne, Laslo Pap and Istvan Szekely It is certified that error appears in the above-identified patent and that said Letters Patent is hereby corrected as shown below:

Column 30,
Line 5, -- 300 I/ha -- instead of "300 I/ha"

Column 36,
Formula V, -- $D\text{-}(CR^5R^6)_0 - (CR^7R^8)_p - C\equiv C\text{-}E$ -- instead of "$D\text{--}(CR^5R^6)_0 - (CR^7R^8)p - C\equiv C\text{--}$"

Signed and Sealed this

Ninth Day of July, 2002

Attest:

Attesting Officer

JAMES E. ROGAN
Director of the United States Patent and Trademark Office